United States Patent
Czaja

(10) Patent No.: US 9,673,864 B2
(45) Date of Patent: Jun. 6, 2017

(54) WIRELESS HIERARCHICAL HETEROGENEOUS PICO-NET FOR SKI CONTROL SYSTEMS

(71) Applicant: Stanislaw Czaja, Cardiff, CA (US)

(72) Inventor: Stanislaw Czaja, Cardiff, CA (US)

(73) Assignee: IPCOMM, Cardiff, CA (US)

( * ) Notice: Subject to any disclaimer, the term of this patent is extended or adjusted under 35 U.S.C. 154(b) by 172 days.

(21) Appl. No.: 14/658,180

(22) Filed: Mar. 14, 2015

(65) Prior Publication Data
US 2015/0249482 A1    Sep. 3, 2015

Related U.S. Application Data

(63) Continuation-in-part of application No. 14/065,060, filed on Oct. 28, 2013, now Pat. No. 9,020,782.

(51) Int. Cl.
*H04B 5/00* (2006.01)
*H04L 12/863* (2013.01)
(Continued)

(52) U.S. Cl.
CPC ......... *H04B 5/0031* (2013.01); *A43B 1/0054* (2013.01); *A43B 3/0005* (2013.01);
(Continued)

(58) Field of Classification Search
CPC ......... A63C 9/00; A63C 5/06; A63C 2203/22; A63C 2203/18; A43B 3/0005; A43B 5/0415; G06F 19/3481; G05D 19/02
(Continued)

(56) References Cited

U.S. PATENT DOCUMENTS 6,498,994 B2 * 12/2002 Vock ............... A42B 3/0433
702/141
6,690,657 B1 * 2/2004 Lau ............... H04B 7/15542
370/315
(Continued)

FOREIGN PATENT DOCUMENTS

CN    203851143 U * 9/2014

*Primary Examiner* — Carol S Tsai

(57) ABSTRACT

A wireless hierarchical heterogonous pico-net providing communication between smart-phone based analysis and control application and multiplicity of sensors and actuators embedded in the ski equipment is described. The topology of this pico-net comprises two layers of hierarch, where the first layer is configured as a Bluetooth wireless network using a Round-Robin scheduling method and consisting of a single master and up-to seven slaves, and the second layer of the hierarchy is configured as a sub-nets consisting of multiplicity of sensors and actuators and communicating internally using ANT personal area network (PAN) wireless interface, or via a digital wire interface. Such network topology provides deterministic latency of a hierarchy a single-hop Bluetooth network, irrespective of the numbers of sensors and actuators embedded within each sub-net of the second layer of hierarchy. The network latency is upper-bounded by the number of slaves in the first layer of hierarch, Furthermore, the Round-Robin scheduling method is supplemented with the gating-off the slave RF transmission when the slave has no data to send, or when the difference between current sensor samples and the previous sensor sample is smaller then predefined threshold. Such discontinued transmission lowers slave power consumption system interference.

19 Claims, 23 Drawing Sheets

(51) Int. Cl.

| | |
|---|---|
| *H04W 4/00* | (2009.01) |
| *H04W 4/04* | (2009.01) |
| *A43B 3/00* | (2006.01) |
| *A43B 5/04* | (2006.01) |
| *A63C 5/06* | (2006.01) |
| *A43B 1/00* | (2006.01) |
| *H04W 84/20* | (2009.01) |
| *A63C 9/00* | (2012.01) |
| *G06F 19/00* | (2011.01) |

(52) U.S. Cl.
CPC ............. *A43B 5/0415* (2013.01); *A63C 5/06* (2013.01); *H04L 47/6225* (2013.01); *H04W 4/008* (2013.01); *H04W 4/04* (2013.01); *A63C 9/00* (2013.01); *A63C 2203/18* (2013.01); *A63C 2203/22* (2013.01); *G06F 19/3481* (2013.01); *H04W 84/20* (2013.01); *Y02B 60/50* (2013.01)

(58) Field of Classification Search
USPC ....... 702/72, 19, 44, 60, 160, 182, 141, 149, 702/187, 188; 422/101, 72, 63; 436/43
See application file for complete search history.

(56) References Cited

U.S. PATENT DOCUMENTS

| | | | | |
|---|---|---|---|---|
| 6,870,300 | B2 * | 3/2005 | Bolle | G02B 6/357 310/309 |
| 7,072,789 | B2 * | 7/2006 | Vock | A63C 5/06 482/8 |
| 7,289,821 | B2 * | 10/2007 | Kim | H04L 12/423 370/230 |
| 8,239,146 | B2 * | 8/2012 | Vock | A42B 3/046 702/44 |
| 2004/0166883 | A1 * | 8/2004 | Kim | H04L 12/423 455/512 |
| 2007/0076672 | A1 * | 4/2007 | Gautier | H04W 84/20 370/338 |

\* cited by examiner

WIRELESS HIERARCHICAL HETEROGENEOUS PICO-NET FOR SKI CONTROL SYSTEMS

PRIORITY INFORMATION

This application is a Continuation in Part application of non-provisional application Ser. No. 14/065,060 titled "Adaptive Vibration Control for Ski" filled Oct. 28, 2013, which was a Continuation in Part of a non-provisional application Ser. No. 13/024,070 titled "Wireless System for Monitoring and Analysis of Skiing" filled on Sep. 2, 2011, now U.S. Pat. No. 8,612,181 which claimed the benefit of priority under the 35 U.S.C. section 119 of Provisional Application No. 61/310,584 titled "Wireless System for Monitoring and Analysis of Skiing" filed Mar. 4, 2010, which are hereby incorporated by reference in their entirety as though fully and completely set forth herein.

FIELD OF THE INVENTION

The present invention relates to the field of wireless communication and specifically a wireless pico-net for communication between the monitoring and analysis application and a multiplicity of sensors embedded in the ski equipment. Such wireless pico-cell network carries sample data from MEMS (Micro-Electromechanical System) accelerometer sensors embedded in the ski equipment to the monitoring and analysis application residing in the skier smart-phone and a control data generated by the monitoring and analysis application to the MAMS actuators embedded in the ski equipment. Such system provides a real-time analysis of skiing activities, such as: monitoring skier body position and forces he or his equipment is experiencing; provide new level of safety; enhance skiing experience and performance. The processed data from accelerometers are used to calculate moments applied to the user body and equipment, then a corrective feedback is sent to the actuators embedded in the equipment. Among other, such corrective action may consist of: changing the tension (extend or shorten) of the ski edge to aid in edge handling; change the torsion of a selected parts of the ski; damping vibration of the ski; and release of the ski bindings when moments applied to the skier leg exceeds safety limits.

To satisfy the requirements of such system a secure, robust and low power short range wireless network with low latency and the ability to address multiplicity of sensor and actuators at the single level (single-hop) network topology is needed. Such network must be compatible with the wireless Personal Area Network, or Body Area Network technologies such as: Bluetooth, ANT, ZigBee, NFC, etc.

BACKGROUND

Currently monitoring of skier/skiing performance relies on few techniques, such as: skier feelings, instructor/coach observations, etc, and some empirical factors, such as: time measurements, post run video analysis, while the safety and comfort depends on decades old ski binding technology, incremental progress in materials and manufacturing technology. Some analytical methods for data collection during the development phase of the ski equipment are in use today, however, most of those techniques are not practical for the every day training of professional or recreational skier, as they require bulky equipment and require large team of highly skilled technicians to operate.

It is well known that the safety of skiing depends predominantly on ski bindings. Currently, binding safety is defined by the stiffness of it's spring(s) used to hold/release ski boot, which is adjusted according to the presumed capability of the user and the user weight. This basic principle of ski binding didn't changed in past 40 years (also many incremental improvements, such as: multi-pivots/springs were added), and perform satisfactory most of the time—when the speeds are modest, the spring pre-set torque was below the critical level and the user is physically fit, the fundamental problem—relying on intuition for setting the spring strength and fact that in almost all cases, only one of the binding, the one experiencing excessive force, will release. This is mainly to the fact that the forces applied to both skis and/or skis trajectory are not the same. In effect, while one ski is released the other, the other is still attached to the user causing serious injuries during a fall.

The comfort and safety of skiing is also affected by excessive ski vibration. Such vibrations are an effect of the moments applied to the ski edge by skier body position in relation to ski slope when the ski turns, especially on a hard icy snow or moguls. Since part of skiing experience is related to turns, manufacturers introduced skis with strong sideline curvature—broader tip and tail and narrow center, and high flexibility. Unfortunately, such design leads to large vibration amplitudes, so skis are manufactured with different stiffness factor to balance the needs and experience of broad range of skiing enthusiasts, from beginners to professionals. In effect, soft and highly flexible skis, targeting average expertise levels and/or soft snow have tendencies to vibrate excessively at high speeds or in tight turns or hard or icy snow, while less flexible or stiffer skis, targeted for experts are difficult to control by an average skilled user. However, all skis, regardless of their design parameters will vibrate in turns does loosing the edge contact with the snow making edge control difficult and increases discomfort and decreases safety and performance.

Depending on the speed and snow condition, ski vibrates at several bending and torsional frequencies with the amplitudes of such vibration dependent on ski construction—stiff and hard ski may have lower amplitudes at some frequencies but are difficult to control by an average user, while soft ski may be easy to control but have higher vibration amplitudes. In general, the ski bending frequencies are between 10 Hz and 100 Hz, while the torsional frequencies are in the range of 100 Hz to 150 Hz.

For several decades designers try different materials, manufacturing techniques and vibration damping schemes to somehow minimize its negative effect. As the ski vibrates predominantly at the front and the tail quarters of its length, various damping materials and structures were added to the front, tip and tail of the ski.

However, adding large amount of damping does not solve this problem while making ski less responsive and slow. It is well know that ski vibrates over relatively wide range of frequencies, and while dampening materials or dampening viscous structures are effective to damp particular frequency, such structures are not efficient in damping wide range of frequencies, and sometime even counterproductive. Ceramic piezoelectric structures were proposed to provide active dampeners, however, since only small amount of strain—as low as 1%, is usable to provide the control signal, they proved to be difficult to control and unstable or require "pre-tension" of the piezoelectric material in proportion to the expected bending forces in order to produce reference signal, and as such not compatible with ski manufacturing technologies.

As the current monitoring systems are not practical for every day use, not only the analysis of the skier run is relegate to post run subjective interpretation, but more significantly the safety of the skier (such as the response of the ski bindings) is left virtually unchanged for the past thirty years, thus also the number of recreational skiers increased, their safety and experience is not improved.

In recent years, the use of mobile devices and, in particular, cellular telephones has proliferated. Today, cellular phone besides providing basic communication over cellular network is equipped with various input/output capabilities, such as wireless PAN (Personal Area Network), and provides significant computing resources. When such computing resources communicate with the remote sensors, such as MEMS accelerometers, magnetometers, gyroscopes, pressure sensors, actuators the resulting system can provide various sport analytical tools for monitoring of v skiing.

By coupling MEMS accelerometers and actuators embedded in the ski equipment with an analysis application residing in the user smart-phone, one can provide tool analyzing forces experienced by the user and increase in safety and comfort of skiing. Furthermore, using the smart-phone connectivity to the wireless cellular network, a real-time feedback to the equipment may be provided to add in ski testing or training, comfort and safety. System described in this invention can operate using any of wireless technology such as: cdma2000, UMTS, WiMax, LTE. LTE-A, etc.

SUMMARY OF THE INVENTION

This invention describes a hierarchical, heterogonous pico-net providing communication between smart-phone based analysis and control application and sensors and actuators embedded in the ski equipment. The topology of this pico-net provides all benefits of Bluetooth radio interface (ubiquitous presence in smart-phones, easy to use, security, etc.), and low latency equal to the latency of a single-hop network. Such latency is irrespective of the numbers of sensors and actuators in the network and upper bounded by the number of slaves in the $1^{st}$ layer of the hierarch, The Round-Robin scheduling scheme is supplemented with the gating-off the slave RF transmission when the slave has no data to send, does lowering slave power consumption and lowering system interference. This network provides communication structure for various skiing analysis, monitoring and control systems, among others: remote monitoring of the skiing performance, analysis and control of ski vibrations or control of adaptive ski bindings.

Such systems consists multiplicity of sensors embedded in the ski equipment and/or attached to the skier, communicating wirelessly with analysis and control application residing in the skier smart-phone. The output of the sensors representing instantaneous changes in acceleration in X/Y/Z axis provide data for calculation of skier position, moments applied to the ski edges and skier body, vibration of the skis and/or forces applied to the ski binding/snow interface.

The results of measurements obtained from such analysis system may be augmented with video capture, GPS supported ski slope mapping system, or radio telemetry or GPS synchronized CCTV systems installed along the ski slope, and the resouts may be transmitted in real-time to the remote location using wireless cellular network (Wireless Metropolitan Access Network), technology.

In one embodiment of ski monitoring and analysis system the MEMS motion sensors such as: accelerometers, gyroscopes, magnetometers, barometric pressure and MEMS actuators are embedded in various locations essential for the measurement of skier performance, such as: skis, ski boots, cloth, poles, gloves, etc. In another embodiment of ski analysis and control system such sensors and actuators are embedded in the skis and/or ski bindings providing data for real-time analysis of ski vibrations and/or forces applied to the ski bindings then after analysis provide control signals to the actuators embedded in the skis and/or ski bindings to damping ski vibration or releasing the ski bindings. As sensors sampling and the application of control signals must satisfy the requirements of real-time control process, the latency of communication network connecting the user smart-phone and the multiplicity os such sensors and actuators must be as small as possible while at the same time it must provide easy and wide deployment, security and resilience to interference.

Many times, such analysis/control system will provide a data link to the remote location using cellular radio interface of the skier smart-phone to provide real-time feedback or to store such data for further analysis.

Such monitoring and analysis systems may be equipped with the graphic rendering and capable of retrieving topological information from a radio-telemetry, GPS or GPS synchronized video from slope installed CCTV cameras, such system can display skier position in relation to the slope does allowing for the real-time analysis (by the coach) or post-run review by the user. Both the real-time and post-run analysis provide recording of all parameters of the run, such as edge forces, acceleration, etc, as well as rendering of skier position vs. slope. Furthermore, the graphical representation of the run can be interpolated between the samples to provide a visual representation of the entire run.

It is well known that ski or snowboard turns when moments are applied to the ski edge by skier body position in relation to ski slope and the skier speed, and the turning performance is determined by the centrifugal force and the reaction to this force introduced by ski-snow contact.

To achieve tight turning radius, the ski sideline edge is curved and ski is made flexible to allow bending during the turn and avoid rolling. To improve the experience of skiing, manufacturers introduced skis with strong sideline curvature—broader tip and tail and narrow center, and high flexibility. In effect, highly flexible skis have tendencies to vibrate excessively at high speeds or in tight turns or hard or icy snow. When ski vibrates, it looses the edge contact with snow making edge control difficult, decreasing comfort, safety and performance.

It is also well known that skiing safety is very much related to skier skills, it is well understood that ultimate safety is proportional to many factors even beyond control of professional skiers. However, the only part of ski equipment dedicated to safety and fundamentally unchanged during almost half century, is a ski binding, still relying on an arbitrary setting of binding spring tension. In most cases, binding settings is related to the user weight and inferred skills, and not to dynamic condition during the ski run.

MEMS accelerometer/actuator subsystem can be delayed as a safety device in the ski bindings for the purpose of instantaneous release of the ski, when moments experienced by the skier body, ski or ski binding exceeds dynamic parameters determined to be safe by providing a real-time feedback to the MEMS actuator(s) embedded in the ski bindings. Such safety system can be integrated into ski equipment and controlled in a real-time by the feedback mechanism provided by the monitoring application, does providing an additional protection to the user.

System residing in the skier smart-phone and communicating is equipped MEMS sensors and actuators embedded in various position of the ski equipment and performing real-time of forces experienced by the equipment and the skier body may provide visual analysis of run, compensate and correct errors, damp ski vibration to improve comfort and release ski bindings for improved safety.

To allow for such system to operate a special type of wireless Pico-net network and communication protocol is required. This Ski Pico-net must be robust to provide: reliable communication in extreme conditions—snow, shocks, stress, etc.; secure—to avoid tampering and cross-interference with the other user's equipment; low power—to guarantee uninterrupted operations; must be able to address multiplicity of sensors and actuators with a very low latency; and be compatible with the equipment hosting the monitoring and analysis application—smart-phone. A popular smart-phone PAN radio interface—Bluetooth, could satisfy most with the exception: ability access large number of devices with a very low latency.

One skilled in art understands that also many network topologies able to connect hundreds or even thousands devices, may be used in Bluetooth deployment, the fundamental connectivity of a Bluetooth in a pico-cell (or the so called one hop network) is limited to only eight devices—one master plus seven slaves. Furthermore, the Bluetooth Physical Layer operates in a TDD (Time Domain Division) mode with the slot period of 625 μs, in which the odd slots are used for transmission from master to the slave(s) while the even slot are used for transmission from slave(s) the master. Slave which is addressed (pooled) in slot 1 must respond in slot 2, so the latency of accessing single slave in Bluetooth network is equal to 1.23 ms. If the pico-net consist of eight devices (master and seven slaves), the period at which the device addressed in slot 1 is addressed again is $2*7*625=8.75$ ms—time sometime referred as 'Bluetooth frame".

When a Bluetooth network requires more then eight devices, it may be configured in one of many multi-hop topologies, such as: scatter-net, mesh, etc. In such topology, one or more slaves may be shared with another master (or one master may perform both as master and slave), but in such architecture, and the requirement the each device is addressed during each pooling sequence (Round-robin scheduling), the interval at which each device is serviced will increase to Number-of-devices*2*7*625 μs, which delay makes such network unusable for the ski monitoring and control system requiring 10-20 addressable devices per ski.

In the following sections, an adaptive system to control ski vibration is described, then based on the requirements of such system novel Bluetooth network topology and associated communication protocol is described.

BRIEF DESCRIPTION OF THE DRAWINGS

A better understanding of the present invention can be obtained when the following detailed description of the preferred embodiment is considered in conjunction with the following drawings, in which.

Figure 1:
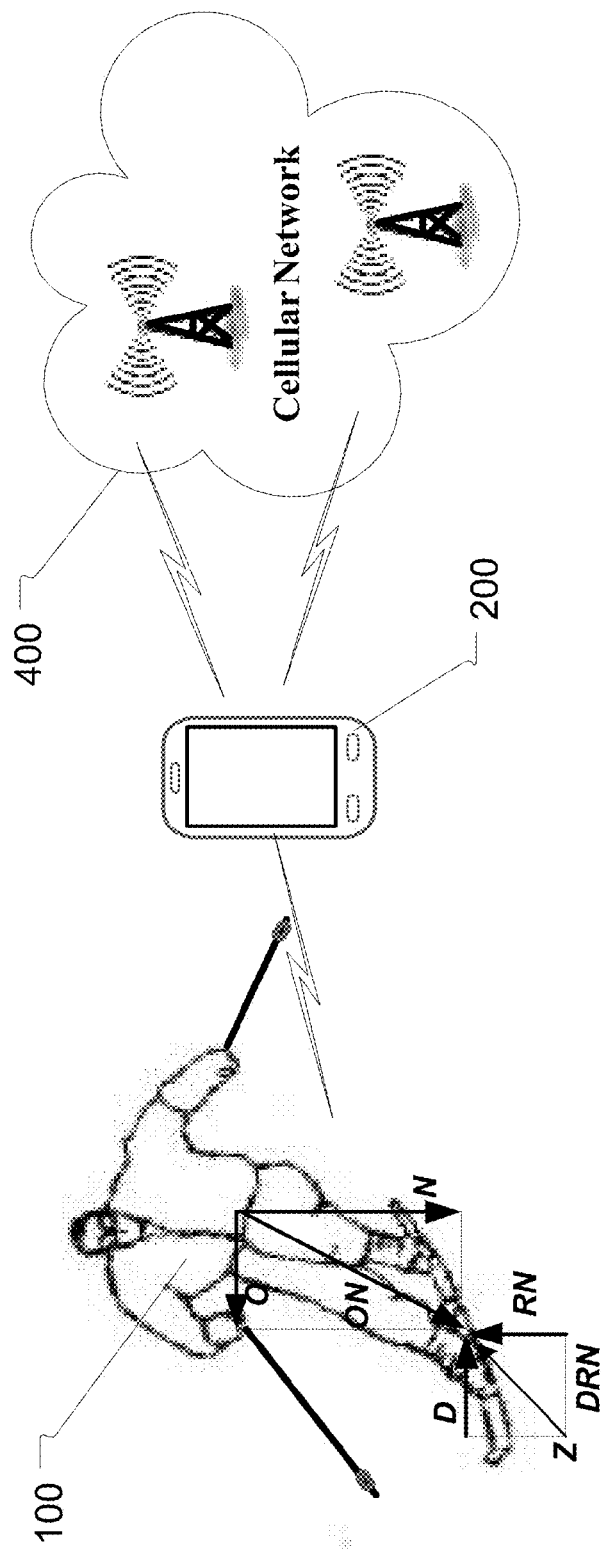
FIG. 1 is an exemplary ski monitoring system.

While the invention is susceptible to various modifications and alternative forms, specific embodiments thereof are shown by way of example in the drawings and are herein described in detail. It should be understood, however, that the drawings and detailed description therefore are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following is a glossary of terms used in the present application:

Active Monitoring System—in the context of this invention a system able to collect various instantaneous vectors such as, acceleration, angular orientation, geo-location and orientation, then using various angulation and mathematical operations calculate the forces applied to various areas of sport equipment or the user body then send commands to actuators embedded in the sport equipment to provide corrective action.

Application—the term "application" is intended to have the full breadth of its ordinary meaning. The term "application" includes 1) a software program which may be stored in a memory and is executable by a processor or 2) a hardware configuration program useable for configuring a programmable hardware element.

Coach—in the context of this invention, any person authorized by the user to receive the data from the user monitoring system and provides analysis in real-time or off-line of the user performance.

Computer System—any of various types of computing or processing systems, including mobile terminal, personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Mobile Terminal—in the scope of this invention any wireless MAN enabled terminal such as cell-phone, smart-phone, etc.

Memory Medium—Any of various types of memory devices or storage devices. The term "memory medium" is intended to include an installation medium, e.g., a CD-ROM, floppy disks 104, or tape device; a computer system memory or random access memory such as DRAM, DDR RAM, SRAM, EDO RAM, etc.; or a non-volatile memory such as a magnetic media, e.g., a hard drive, FLASH or optical storage. The memory medium may comprise other types of memory as well, or combinations thereof. In addition, the memory medium may be located in a first processor in which the programs are executed, or may be located in a second different processor which connects to the first processor over a network, such as wireless PAN or WMAN network or the Internet. In the latter instance, the second processor may provide program instructions to the first processor for execution. The term "memory medium" may include two or more memory mediums which may reside in different locations, e.g., in different processors that are connected over a network.

NFC—in the scope of this invention a type of radio interface for near communication.

PAN—in the scope of this invention, a personal are network radio interface such as: Bluetooth, ZigBee, Body Area Network, etc.

Passive Monitoring System—in the scope of this invention a system able to collect various instantaneous vectors such as, acceleration, angular orientation, geo-location and orientation, then using various angulation and mathematical operations calculate the forces applied to various areas of sport equipment or the user body to provide on-line or off-line analysis of the user performance.

QR-code—Quick Response Code, a 2-D bar code

Ski Equipment—in the context of this invention, any part of equipment used by the skier, such as: skis, ski boots, ski poles, ski clothing, ski glows, etc.

Ski Equipment Parameters—in the context of this invention, ski or snowboard design and manufacturing parameters, such as: length, weight, toe/center/tail, stiffness, are extracted after manufacturing and entered into application.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Topological Information—in the context of this invention, information about the topology of the ski slop obtained through any combination of techniques such as: topography maps, GPS, Radio-Telemetry, barometric pressure monitoring, etc.

User—in the context of this invention, skier using the monitoring system.

Vibration Control System—in the context of this invention a system able to collect various instantaneous vectors such as, acceleration, angular orientation, etc., then using various mathematical operations calculates resonance frequencies of vibrating ski then sends commands to actuators embedded in the sport equipment to provide corrective action.

WMAN—Wireless Metropolitan Access Network such as cellular network.

ANT Wireless Network—ANT is an open access wireless sensor network protocol and RF solution that operates in the unlicensed 2.4 Ghz ISM band, and designed for ultra-low power Personal Area Networks.

Bluetooth Frame—in the context of this invention, a time period required to address a single slave in a Bluetooth network and equal to two consecutive time slots.

Bluetooth Meta-frame—in the context of this invention, a time period required to address the same slave while using a Round-Robin scheduling algorithm and equal to $2*N*625$ µs, where N=number of slaves and 625 µs period is the time of a single Bluetooth slot.

One-hop Network—in the context of this invention, a network with only path between the source and destination.

Multi-hop Network—in the context of this invention, refers to the number of intermediate devices (like bridge between to pico-nets) through which data must pass between source and destination and the hop count of n means that n gateways separate the source host from the destination.

Gated-off Transmission—in the context of this invention a slot period scheduled for slave, during which the slave disables it's transmitter and the master recognized the absence of such transmission as a 'null' content.

The following sections presents a two embodiments of a ski monitoring system which benefit from the wireless network designed to provide the connectivity between the multiplicity of sensors and actuators embedded in the ski equipment.

Skiing Monitoring and Analysis

A skiing monitoring and analysis system leverages on the properties of wireless Personal Area Network (PAN) such as Bluetooth and wireless wide area network, such as a cellular network, and combines the inherent benefits provided by those networks with the sensing technology such as: MEMS accelerometers, gyroscopes, magnetometers, actuators, embedded into skier equipment and an application software residing in the personal wireless terminal (for example user smart-phone).

In this invention sensor technology embedded in various places of the user ski equipment, provides instantaneous measurements of various moments applied to the skier body and his equipment to a mobile terminal based monitoring application over the PAN wireless interface. These measurements in addition to topological and location information (obtained from preloaded slope maps, GPS, Galileo, radiotelemetry, etc.), as well as user physical parameters, such as: weight, heights, distance from ankle to knee and hip, etc, and ski physical parameters, such as: total length, edge length and radius, etc. are used by the monitoring application to provide piece-wise analysis of the user run.

Since the ski edging is created by tipping (inclining) different parts of the skier body: feet/ankles, lover legs/knees, upper legs/hips and lower spine, then by placing sensors in various positions of ski equipment and skier body and then continuously recording the instantaneous changes of acceleration in x, y or z axis, one can reassemble the skier position during his run. Then with additional information about user physical characteristics (weight, heights distance from ankle to knee and hip, etc.), compute forces applied to the ski edge and experienced by the skier body.

Assuming moderate sampling rate of 1 kHz and 100 km/h speed, the exact skier position in regarding to the slope and ski as well as forces he applies to the ski edges and forces his body is experiencing, are calculated every 2.8 cm along the length of his run.

These piece-wise data are interpolated to provide continuous picture of the run and when superimposed over the graphical representation of the user, it provides realistic graphical representation of the run associated with the information obtained during the analysis.

Such graphical representation with corresponding moments may be reviewed in a real-time and transmitted to the coach wireless terminal, who in turn can feed back the advice to the user over the same wireless link or any other means of communication, or may be transmitted over such wireless network to the server for future off-line analysis, or may be stored locally within the monitoring application RAM.

Further improvements are possible when such monitoring/analysis system is augmented with the feedback mechanism providing commands to MEMS actuators placed inside the ski equipment. Such actuators can change the forces applied to the ski edge be extending or contraption of the ski edge length, provide vibration damping mechanism or instantaneous release of the ski/ski boot connection when certain dynamic forces are present.

Figure 2:
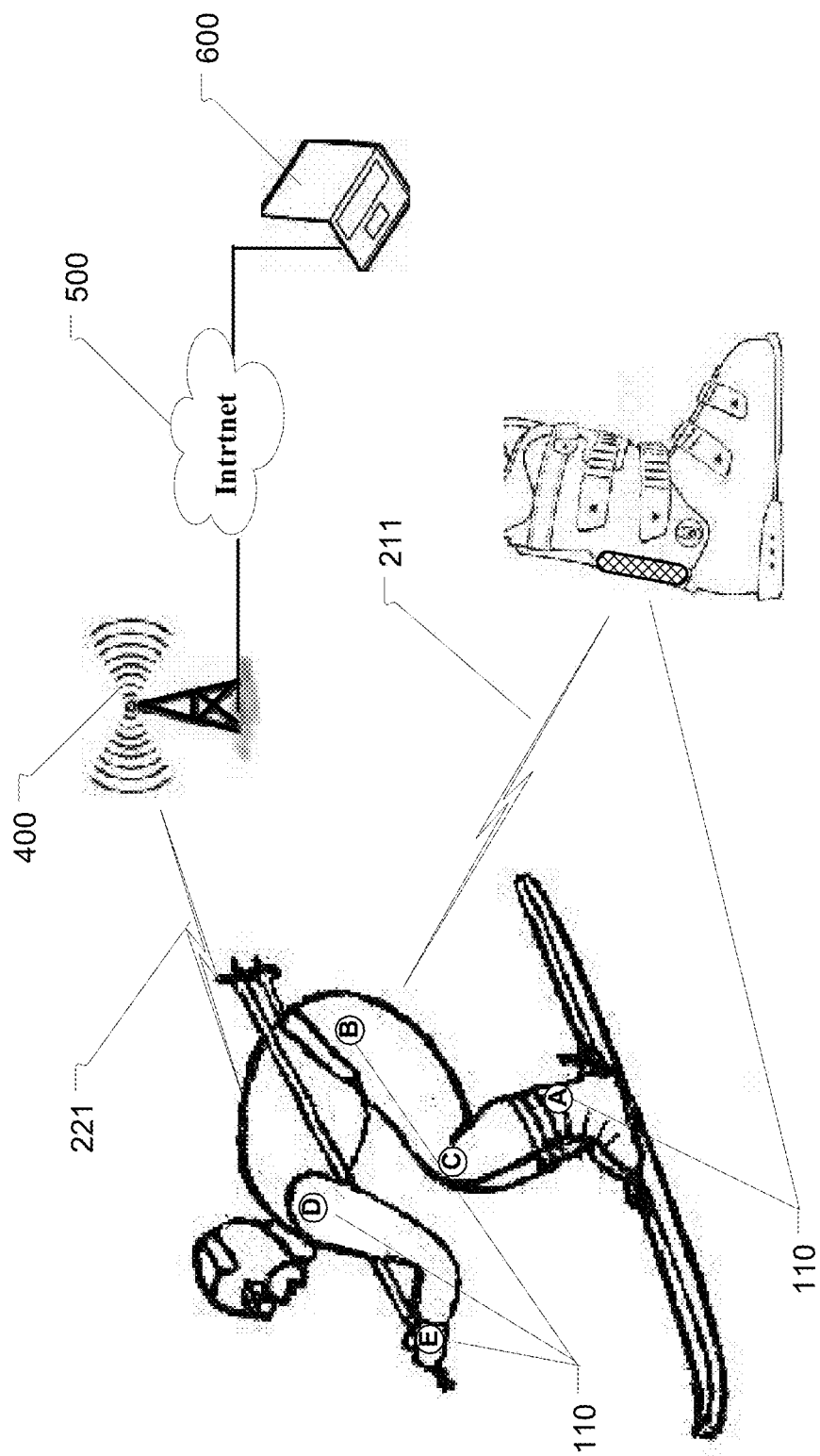
FIG. 2 depicts an exemplary location of the monitoring sensors and communication means.
Figure 3:
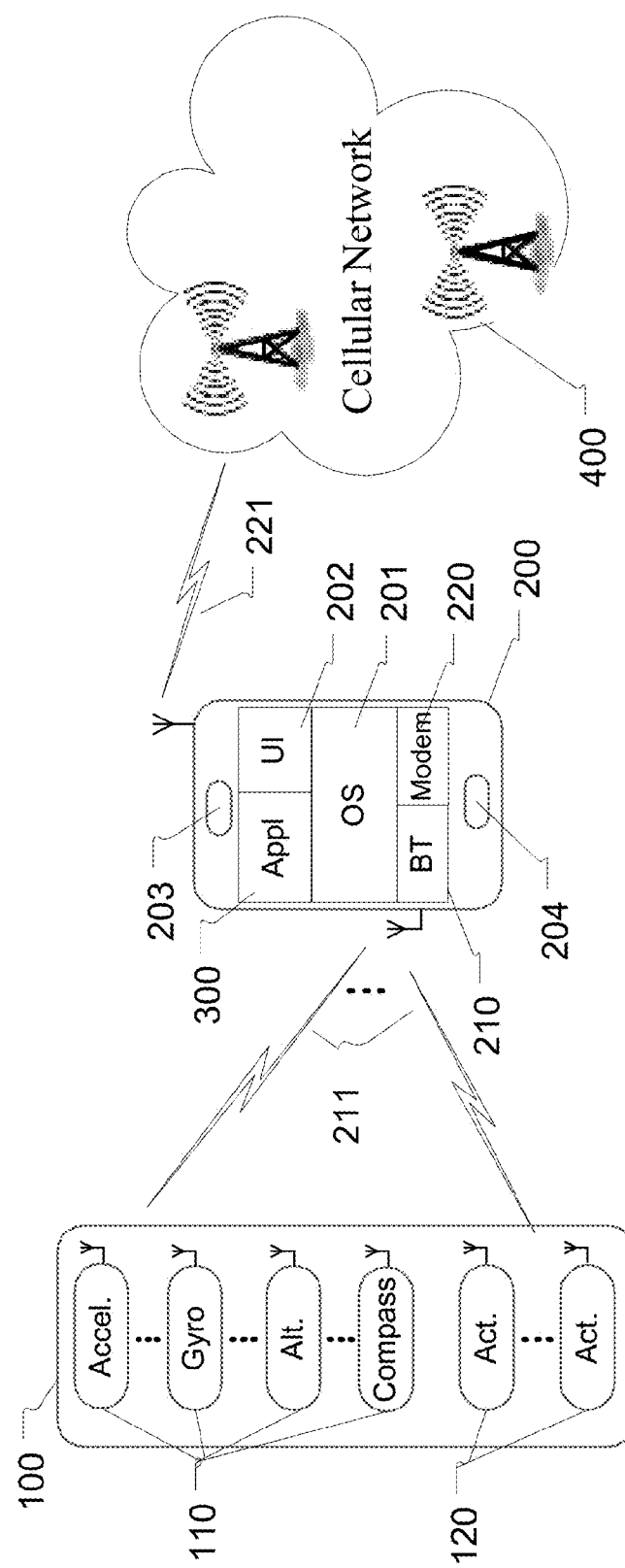
FIG. 3 presents an exemplary architecture of the monitoring system.

An example of such system is presented in FIG. 1 and FIG. 2 and FIG. 3. Here, the monitoring application is embedded into the mobile terminal 200 and communicates with the monitoring subsystem 100 consisting of MEMS sensors 110 and MEMS actuators 120 using short range PAN wireless network 211. The mobile terminal 200 is connected to the analysis application 600 through the wireless MAN link 221 and/or Internet network 500.

Sensor 110 of FIG. 2 such as MEMS accelerometer, gyroscope, magnetometer, altitude-meter, etc. is embedded in various strategic places of the ski equipment and/or skier clothing. Those sensors measure predefined parameters such as accelerations in x/y/z axis, barometric pressure, changes in the earth magnetic field etc. Such measurements are sampled at the predefined for particular application and activity rate (i.e. 5 kHz for professional skier and 500 Hz for recreational skier), then transmitted to monitoring application 300 residing within the mobile terminal 200.

Figure 4:
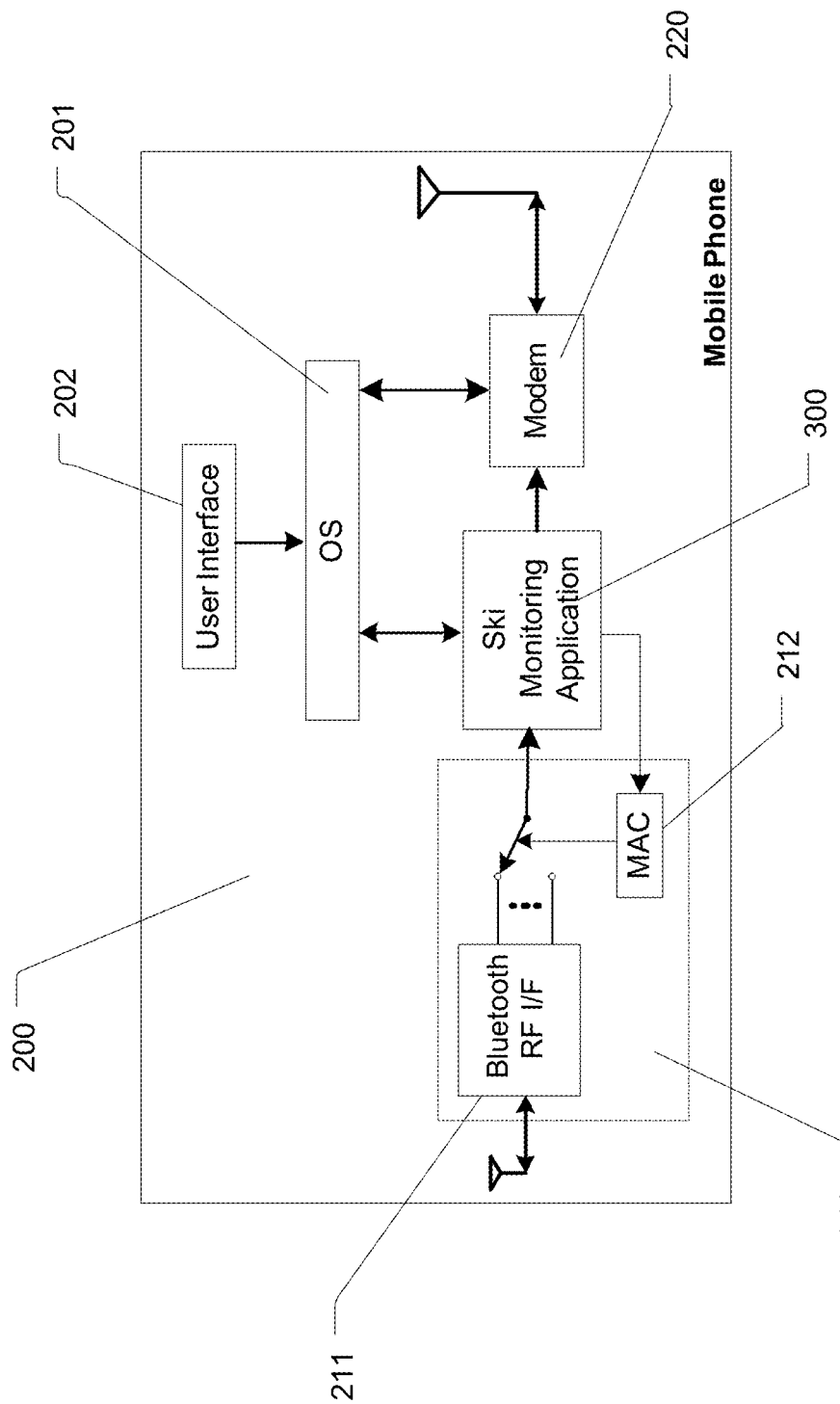
FIG. 4 presents the block diagram of the monitoring application residing within user mobile terminal.

The exemplary monitoring application 300 of FIG. 4 resides within the wireless terminal 200 which consist of short range wireless interface 210, such a Bluetooth, communicating with the sensor/actuator sub-system over wireless link 211 a wireless modem 220 communicating with the MAN network over wireless link 221, a modem OS (Operating System) 201, and the user interface 202.

At the predefined sampling rate the monitoring application 300 sends command to the PAN Media Access Layer (MAC) 211 requesting current measurements. In response the MAC layer retrieves data from each sensor in sensors using RF interface 211, than transfers such data into the monitoring application memory.

Figure 5:
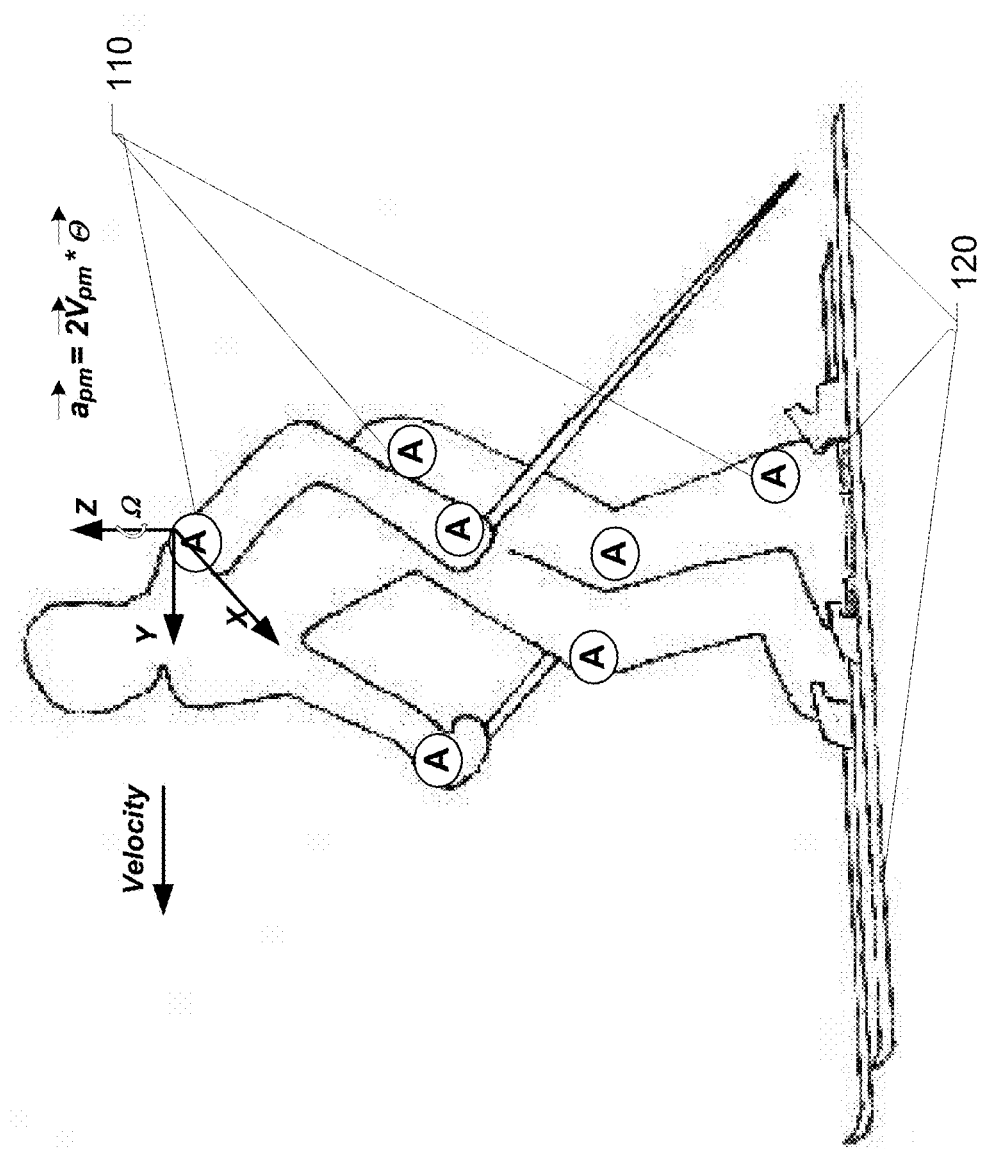
FIG. 5 depicts an example of vectors monitored by various sensors.

Various sensors such as accelerometers, gyroscopes, magnetometers 110, of FIG. 5 are assembled in different configurations to provide measurements of instantaneous vectors in x/y/z axis with 3 or 6 degree of freedom does providing a snap-shot of skier movement. Here the sensors placed on the skier body or embedded into clothing provide information of the position of arms, hips, knees, etc. used to calculate position of skier body vs. the slope line.

Figure 6B:
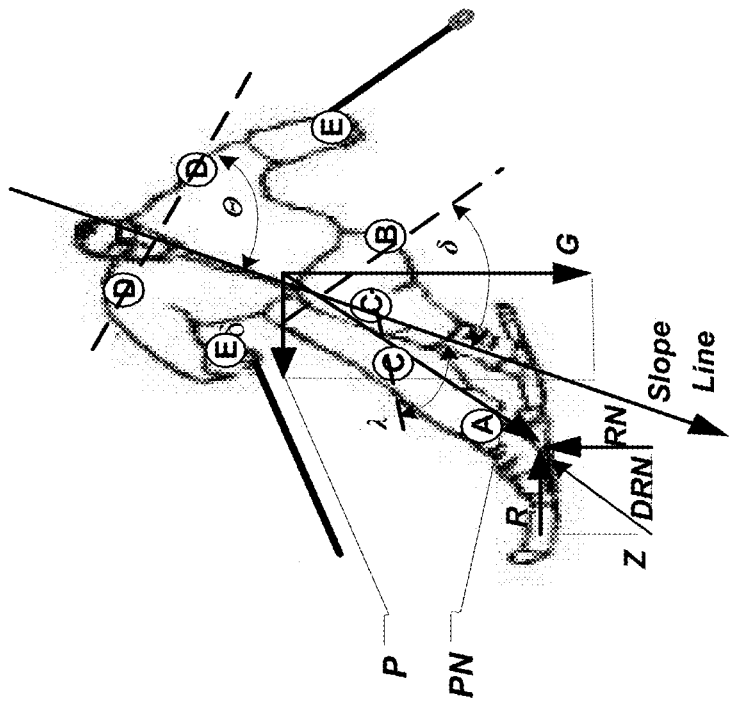
FIG. 6B presents the view of the forces applied to the skier body and the ski equipment in the middle of the turn and their effect on the skier body position.
Figure 6A:
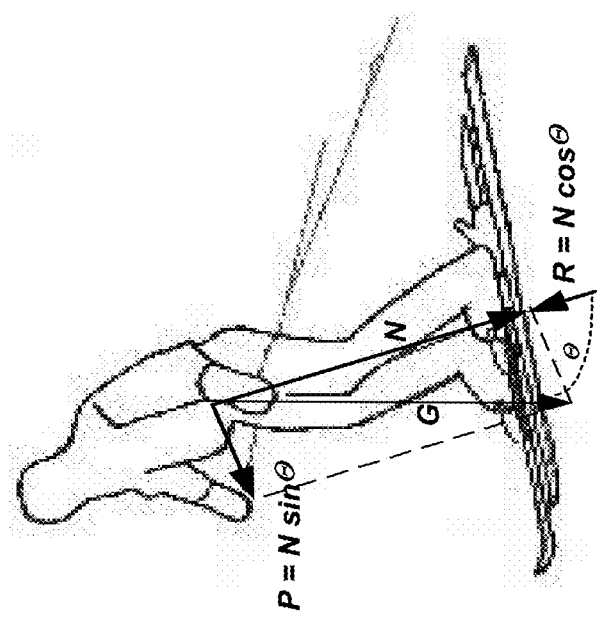
FIG. 6A presents the view of the moments applied by the skier during the initiation of the turn and the effect of such moments on rotation of the ski the skier center mass.

FIGS. 6A and 6B presents method used to calculate forces experienced by the skier body. Here data obtained by sensors D-D are used to calculate changes of angle $\Theta$, between skier shoulder plane and the ski slope; data obtained from sensors B-B are used to calculate changes of angle $\delta$, of skier hips in relation the ski slope; data from sensors C-C, to calculate changes in the angle $\lambda$, of skier knees vs. the ski slope; and data from sensors A-A, to calculate changes in the angle $\phi$, of skis vs. the ski slope and vs. the other ski. When such results are combined with the user physical characteristics (weight, height, knee-hip distance, etc.), one may calculate forces experienced by skier body, such as: rotational acceleration, centrifugal force, forces applied to the ski edges, as well as distance between ski edge and inner turn hip or distance between inner hip and slope among the others. Such calculations may be performed using well known mathematical methods, among others—angulation.

Results of such calculation may be then presented in a form of data tables or graphs and synchronized to the real-time video of the run or superimposed over graphical representation of the user.

The piece-wise representation is post-processed (interpolation, smoothing, rendering, etc), by the analysis application then the entire run is recreated in graphical form or synchronized to teal-time video with forces presented in form of graphs and tables. Such representations can be stored in the wireless terminal local memory for later use, or transmitted over the wireless network 400 to the remote location 600.

Figure 7:
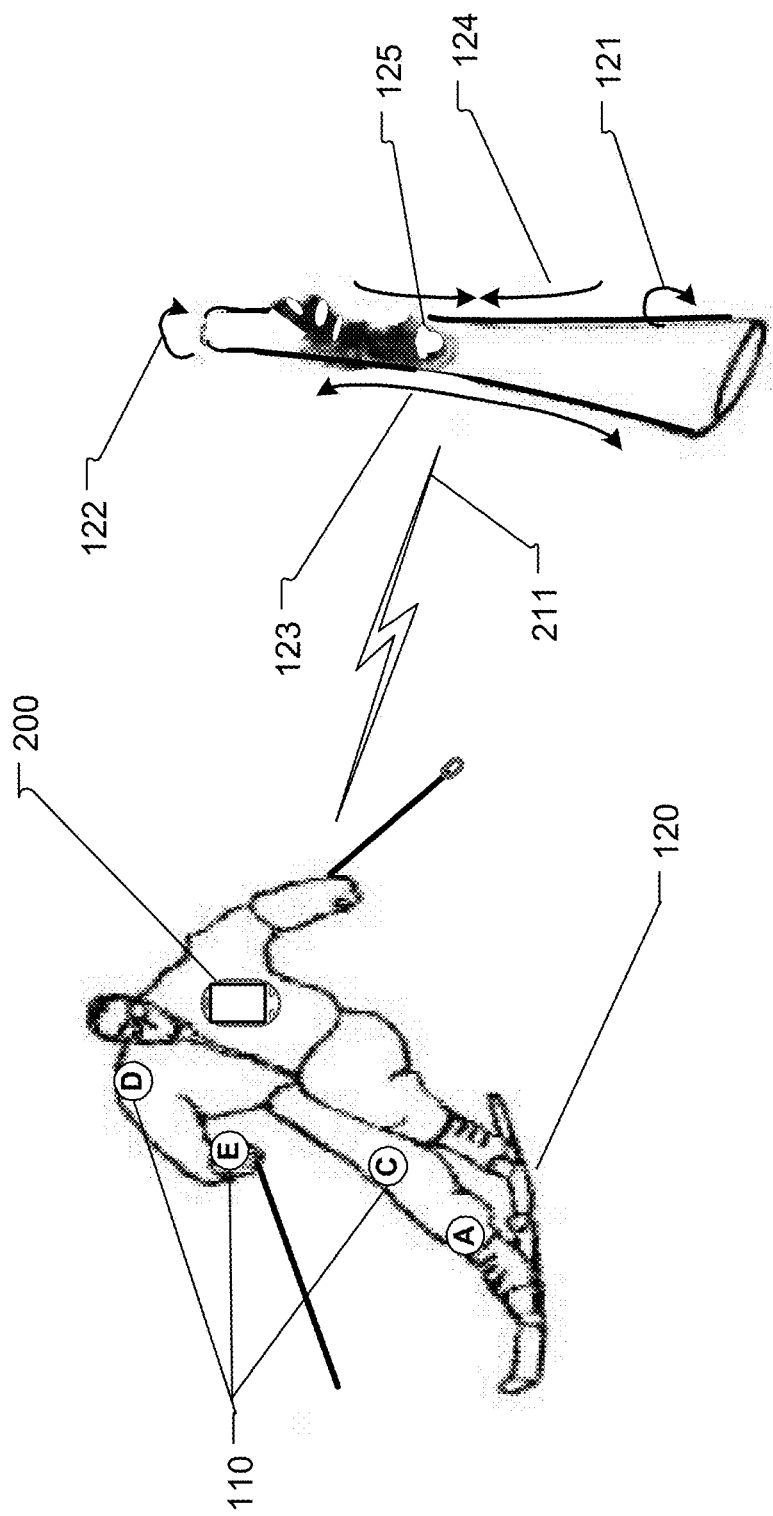
FIG. 7 depicts interaction between the active monitoring system and the ski equipment.

FIG. 7, depicts the analysis application operating in an active mode. Here results of the analysis describe in previous section in reference and FIGS. 5 and 6, are convolved by a correction metric, then the resulting corrective commands are send to the MEMS actuators 120 embedded in various places of the ski equipment. Those corrective commands may for example: change the torque of an particular part of the ski 121 and 122; extend the outer (to the turn) edge of the ski 123, while contracting the inner (to the turn) edge of the ski 124, does improving the ski edge contact and turn performance; dampen excessive ski vibrations; or release the ski binding 125 when the forces experienced by the ski/ski-boot interface exceed predefined safety limits.

The safety parameters of ski/ski-boot interface are calculated every sampling period based on user physical parameters and data from sensors, such as speed, moments applied to certain parts of the skier body, moments on the ski edges, relative (to each other and the slope) ski position, etc. When the instantaneous ski/ski-boot interface value exceeds the dynamic safety threshold for any of the skis a release command is sent to both ski bindings, does eliminating the danger of fall with one ski still attached to the skier leg.

To allow full analysis of the run, beside data received from various sensors, other information specific to the user and his equipment, and if applicable—topology of the run, should be provisioned into application memory.

The first such information may contain user physical parameters, for example: user weight, height, ankle to knee distance, ankle to hip distance, hip to shoulder distance, length of the arm, etc. Such parameters are easy obtained by the user and may be entered among the other methods manually through the mobile terminal UI, or through imaging, by scanning of the QR-code of bar-code or an NFC tag attached to skier clothing.

Additional parameters may include location of the sensors, for example: in skis, ski boots, ski bindings, knee, hip, shoulder, elbow, glove, top of the ski poll, etc. as well as distance between some (or all) of them, for example: distance between ski boot and knee sensor, distance between knee and hip sensor, etc. Such information may be entered into the application manually through the UI or obtained automatically or by other means, such as: scanning of the QR-code or an NFC tag attached to ski equipment, radio ranging, differences in barometric pressure, etc.

The second such information may contain physical characteristics of the ski equipment; such as but not limited to: total ski length and weight, length of the ski edge, turning radius, stiffness/elasticity of various parts of the ski (tip/tail/etc.), ski boots and bindings types and settings, etc. Such parameters may be embedded into the QR-code or an NFC tag attached to the equipment. In addition, when the monitoring application operates in the active mode, the location and type and characteristics of MEMS actuators, for example: edge extension/contraction, vibration damping, etc. tables are included. Such parameters may be obtained from the manufacturer supplied in form of encrypted data files, such as QR-code or an NFC tag attached to the equipment. Such data files can be downloaded over the air during application provisioning by scanning of the QR code or an NFC tag.

The third such information may contain the topological parameters of the ski run such as 3D map(s) or topological contours, etc. Such information can be either preloaded to the application from the ski resort website or downloaded over-the-air automatically when the user transfers from one slope to another based on skier location.

The forth information may contain indication if the topology mapping is supported by the GPS (enough visible satellites plus required accuracy), or radio telemetry system installed along the ski slope or time synchronized (GPS, Galileo, etc) slope CCTV cameras, or barometric pressure transmission capability or any combination of the above. Such information may be obtained automatically by the application when the user enters any specific area.

At each sampling period, vectors from the accelerometers 110, together with the first, second, third and forth information are used by the monitoring application to calculate moments applied to various part of the user body as a moments G, N, P, R, etc., then constructs graphical representation of the user superimposed over the slope topography using information and/or a real-time video. This process is visually presented in FIG. 6, with some of the vectors representing the user position. From those vectors, one can calculate moments applied to ski edge RN and knowing the vector DRN (acceleration along the ski radius), calculate the "skid" along vector D. In a practical system, vectors from multiplicity of sensors (skis, knees, hips, shoulders, hands, etc.) are used to obtain the overall representation of the interaction between skier and the slope.

When the system is operating in the active mode as presented in FIG. 7, after the instantaneous vectors are analyzed a corrective metrics is calculated, then a corrective commands are sent to one or multiplicity of MEMS actuators 120 embedded in the ski or ski bindings over wireless link 211. Such command may change the stiffness of the certain part of the ski 121 and 122, or extend 123, or contract 124 ski edge to enhance ski grip during the turn, or damp temporary vibration of certain part of the ski, or trigger the release of the ski binding 125.

Ski Vibration Control

In this embodiment ski or snowboard vibrations are analyzed, then a corrective signal is generated and sent to the actuators embedded in the ski to cancel such vibrations.

It is well known that ski or snowboard turns when moments are applied to the ski edge by skier body position in relation to ski slope and the skier speed, and the turning performance is determined by the centrifugal force and the reaction to this force introduced by ski-snow contact.

To achieve tight turning radius, the ski sideline edge is curved and ski is made flexible to allow bending during the turn and avoid rolling. To improve the experience of skiing, manufacturers introduced skis with strong sideline curvature—broader tip and tail and narrow center, and high flexibility.

Since such design leads to large vibration amplitudes, manufacturers produce skis with different stiffness factor to balance the needs and experience of broad range of skiing enthusiasts, from beginners to professionals. In effect, soft and highly flexible skis, targeting average expertise levels and/or soft snow have tendencies to vibrate excessively at high speeds or in tight turns or hard or icy snow, while less flexible or stiffer skis, targeted for experts are difficult to control by an average skilled user. However, all skis, regardless of their design parameters will vibrate in turns does loosing the edge contact with the snow making edge control difficult and increases discomfort and decreases safety and performance.

Depending on the speed and snow condition, ski vibrates at several bending and torsional frequencies with the amplitudes of such vibration dependent on ski construction—stiff and hard ski may have lower amplitudes at some frequencies but are difficult to control by an average user, while soft ski may be easy to control but have higher vibration amplitudes. In general, the ski bending frequencies are between 10 Hz and 100 Hz, while the torsional frequencies are in the range of 100 Hz to 150 Hz.

Figure 8:
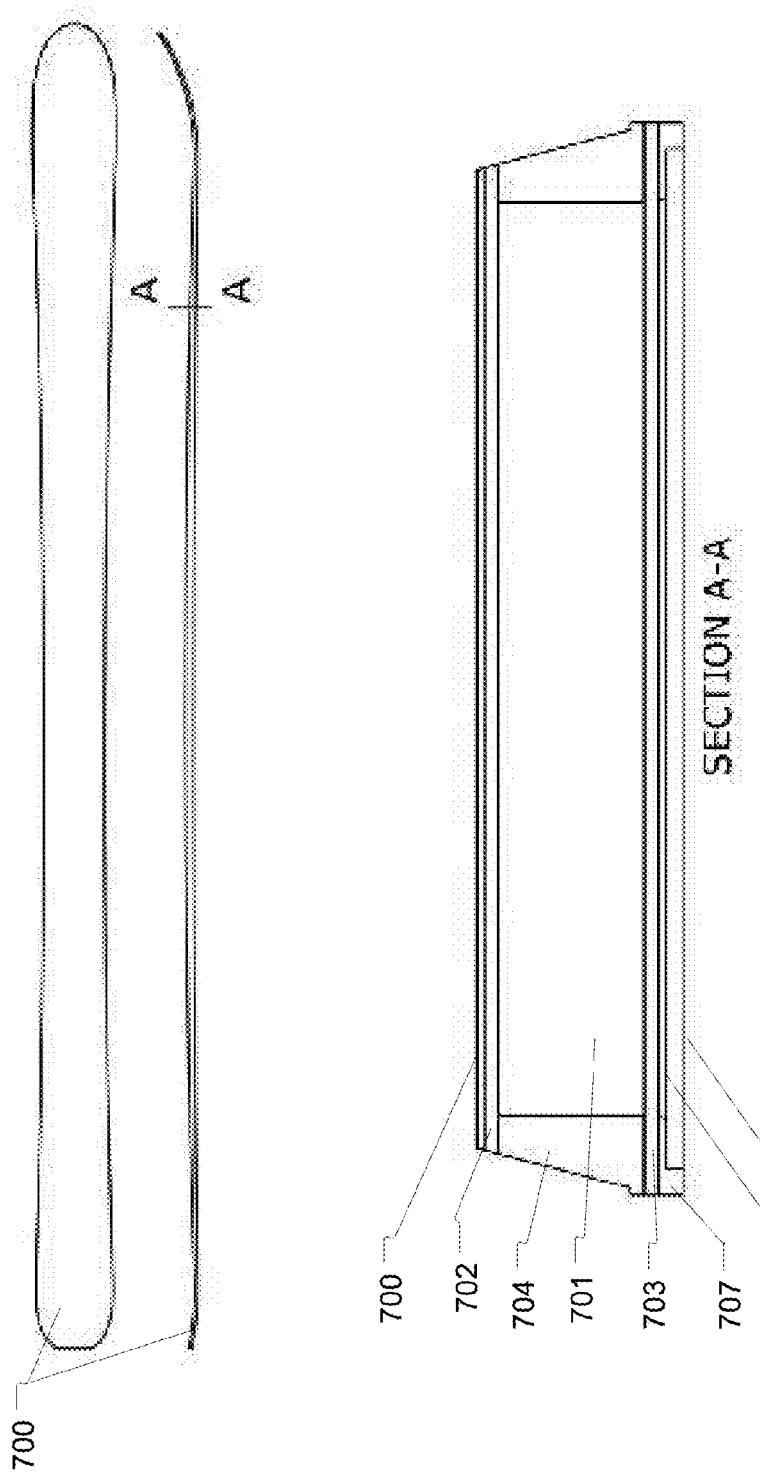
FIG. 8 presents view typical prior-art ski and it's and cross-section.

An exemplary ski 700 of the prior art and it's cross-section A-A is presented in FIG. 8, illustrating the shape and construction of the ski, intended to be structurally strong but flexible and easy to turn.

The core 701, is a central portion of the ski which main function is to provide strength and flexibility and usually made of wood, such as poplar, ash, etc. or honeycomb metal or structural foam. Such core is encapsulated between top 702, and bottom 703 composite layers made of materials such as glass, carbon or carbon-kevlar fibers and ABS sidewalls 704. For a very stiff ski, for example race skis, the composite layers 702 and 703, may be augmented with high tensile strength aluminum alloy layer such as titanal. A layer of fiberglass 705 is added between the lower composite "wrap" of core and the base 706, which provides low resistance sliding on the snow and may be made of sintered polyethylene. The carbon steel edge 707, function is to provide 'grip' to the snow during turns. The main objective of such "sandwich" construction is to provide ski with necessary stiffness while preserving flexibility does allowing easy turns in all snow conditions. Those skilled in art will recognize that the present invention is not limited to the above described ski construction, but may as well be used in other type of skis, such as "cap" or "semi-cap" construction.

Figure 9A:
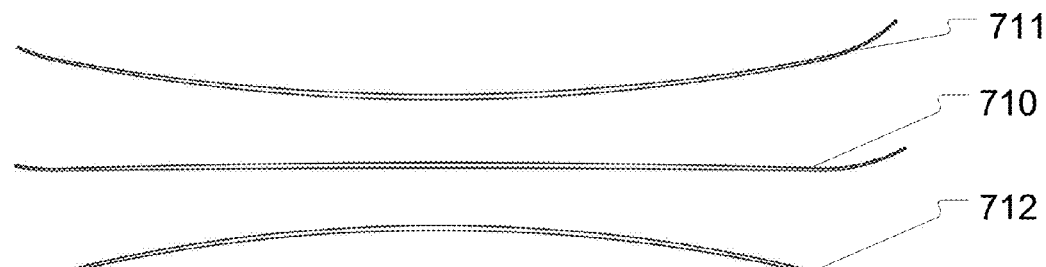
FIG. 9A presents the views of natural ski bending of the ski.

The shape and multi-layer/multi-material construction of ski is intended to provide the strength and ability to bend, such "natural" ski bending: 710, 711 and 712 is presented in FIG. 9A, indicating adaptation to snow conditions are intended to provide continuous contact with the snow and depends on ski design parameters. As such a stiff or racing skis will bend less and will be harder to turn while soft, recreational skis will be more flexible. As such natural bending of the ski is designed to aid in turns, the rate at which the ski bends in the "natural" mode is relatively low and in general below 1-2 Hz, and will be dampened quickly by the parameters of materials used in ski construction. The time domain response of such natural bending vibration of the ski is presented in FIG. 9B, where the vibration amplitude exponential decay function $Xe^{-\zeta\omega_n t}$, 713. The rate of the decay depends on ski construction and is denominated by the damping parameter $\zeta$, 714. As the damping parameter $\zeta$, goes toward unity, the dampening effect is larger as illustrated on FIG. 9C.

When ski travel at higher speeds over hard and/or uneven snow, ski starts to vibrate at several harmonic frequencies, and while the ski traverses from one turn to another, or from one type of ski/snow interface conditions to another, the amplitudes of the bending frequencies may change before it's amplitude decays. When vibration frequency, or their harmonics are similar, or the phase of the amplitudes are equal, such amplitudes will add producing even larger vibrations. The effect of such bending vibration on the ski and it's gliding capability and the induced vibrations in time and frequency domains are presented in FIGS. 10A, 10B and 10C. Such vibrations are mostly pronounced in the tip section of the ski at approximately ½ of the length between the foremost point of ski contact with the snow and the tip of the ski boot, or generally in the area where the ski cross-section is smallest.

Figure 10A:
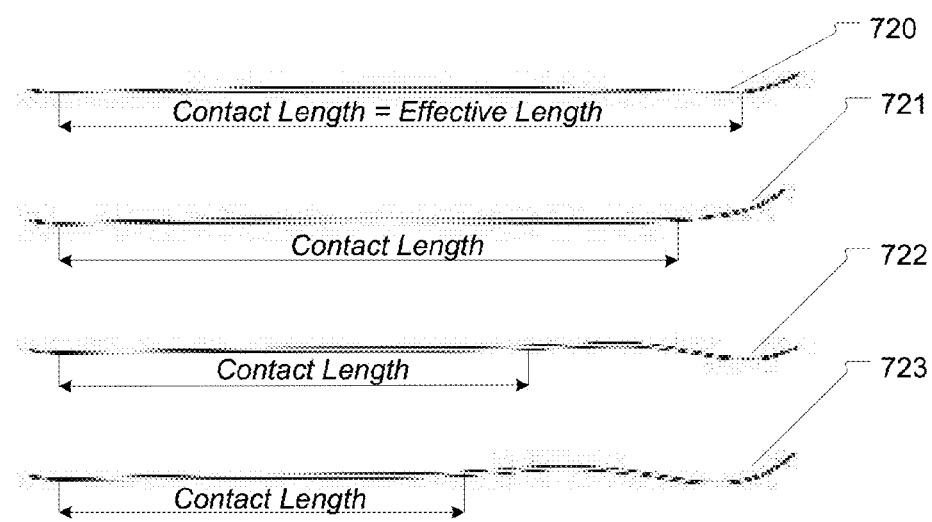
FIG. 10A presents the ski bending due to vibration.
Figure 10B:
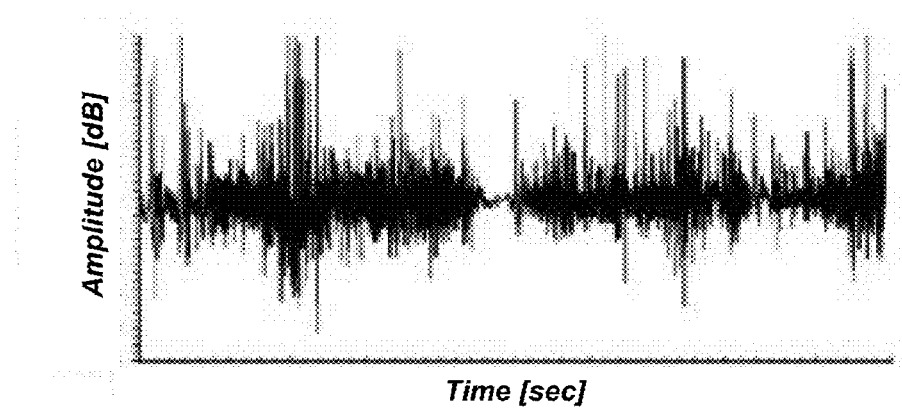
FIG. 10B is a time domain representation of amplitude and frequencies ski vibration as measured during typical run.
Figure 10C:
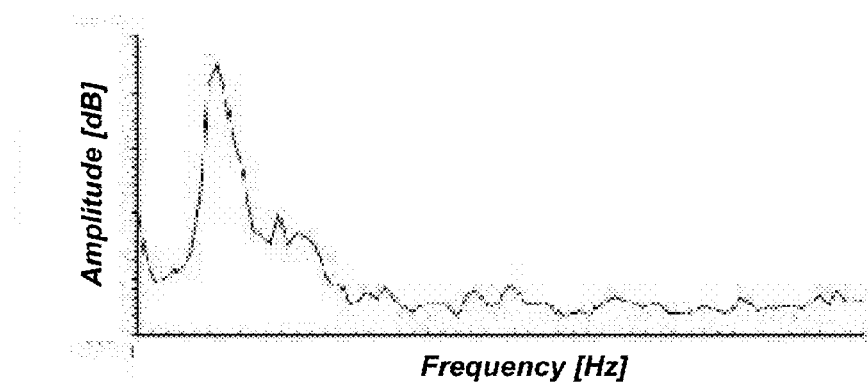
FIG. 10C presents vibration obtained from FIG. 10B after frequency domain analysis showing the power spectral density (PSD) of the vibration.

As seen in FIG. 10A, vibration free ski 720, maintains contact with the snow along it's full effective length. However, when the vibration induced bending force lifts the tip of the ski upwards 721, the entire front portion of the ski looses contact with the snow, making sharp turn ineffective or even impossible. When the natural ski flexibility reacts to such bending force, ski will flex in the opposite direction 722, at which period front of the ski obtains contact with the snow while part between the front and center will loose such contact. In addition of having similar effect on efficiency of the turn as bending, such moment transfers vibration energy to the center of the ski and to skier legs/body, does producing discomfort, making next turn more difficult. In some condition, ski vibration may cause the ski to bend in a shape of wave 723, and hard to control even by very experienced individual. FIG. 10B, presents time domain waveform of such destructive vibration, as FIG. 10C, presents the power density function of such vibration, from which we can see the vibration power (amplitude) is concentrated at approximately 22 Hz.

After analysis vibration induced bending and torsional forces may be controlled and canceled entirely by providing feedback to the actuator sub-system embedded in the ski presented in FIGS. 11 through 18 and described below in details.

Figure 11:
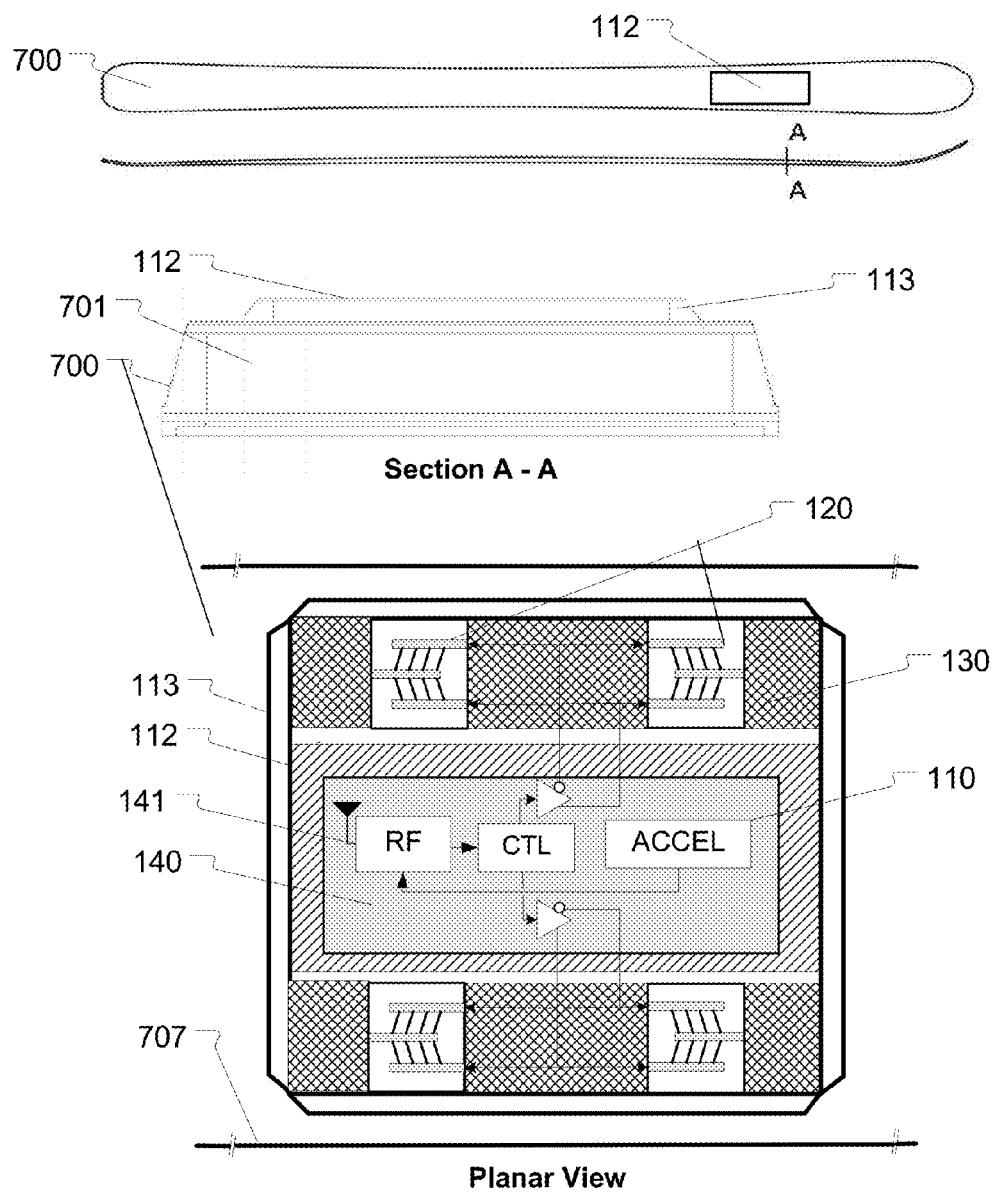
FIG. 11 presents top, side, the A-A cross-section and the planar views of an exemplary ski with the actuator sub-system attached to the top surface of the ski according to the preferred embodiment of the vibration control system.
Figure 12:
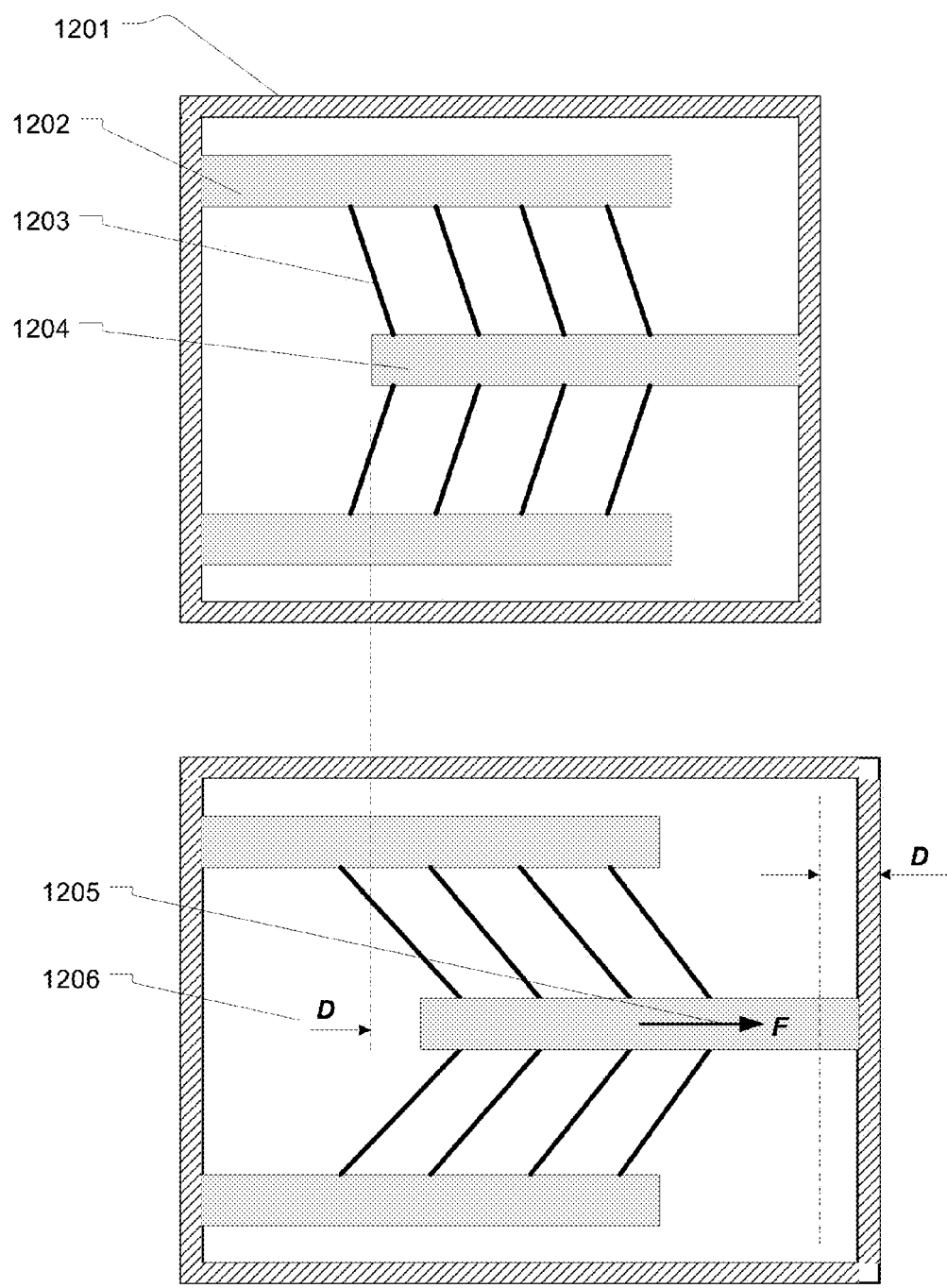
FIG. 12, presents and exemplary view of an exemplary thermo-electrical MEMS actuator in the top view presenting the actuator's shuttle position before application of the control signal, and the bottom view after the application of such control signal, when the shuttle extends due to the Joule effect.

FIG. 11 presents the ski 700, with the attached actuator sub-system 112 according to one embodiment of the actuator sub-system. Here an A-A cross-section of said ski and the actuator sub-system, and a planar view of the actuator sub-system components. The actuator sub-system 112 is hermetically encapsulated in the carbon-kevlar composite structure 113, and consists of actuators enclosure containing, preferably thermo-electric MEMS actuators 120. Such thermo-electric MEMS actuators are compatible with ski manufacturing processes, extremely reliable and provide large forces and displacements, when stacked together. Displacement core 130, transfers moment produced by the expansion/contraction of the actuator to the large area of the ski. In addition, such actuator sub-system may consist control logic 140, accelerometer(s) 110, and a Bluetooth radio interface 211.

Figure 13:
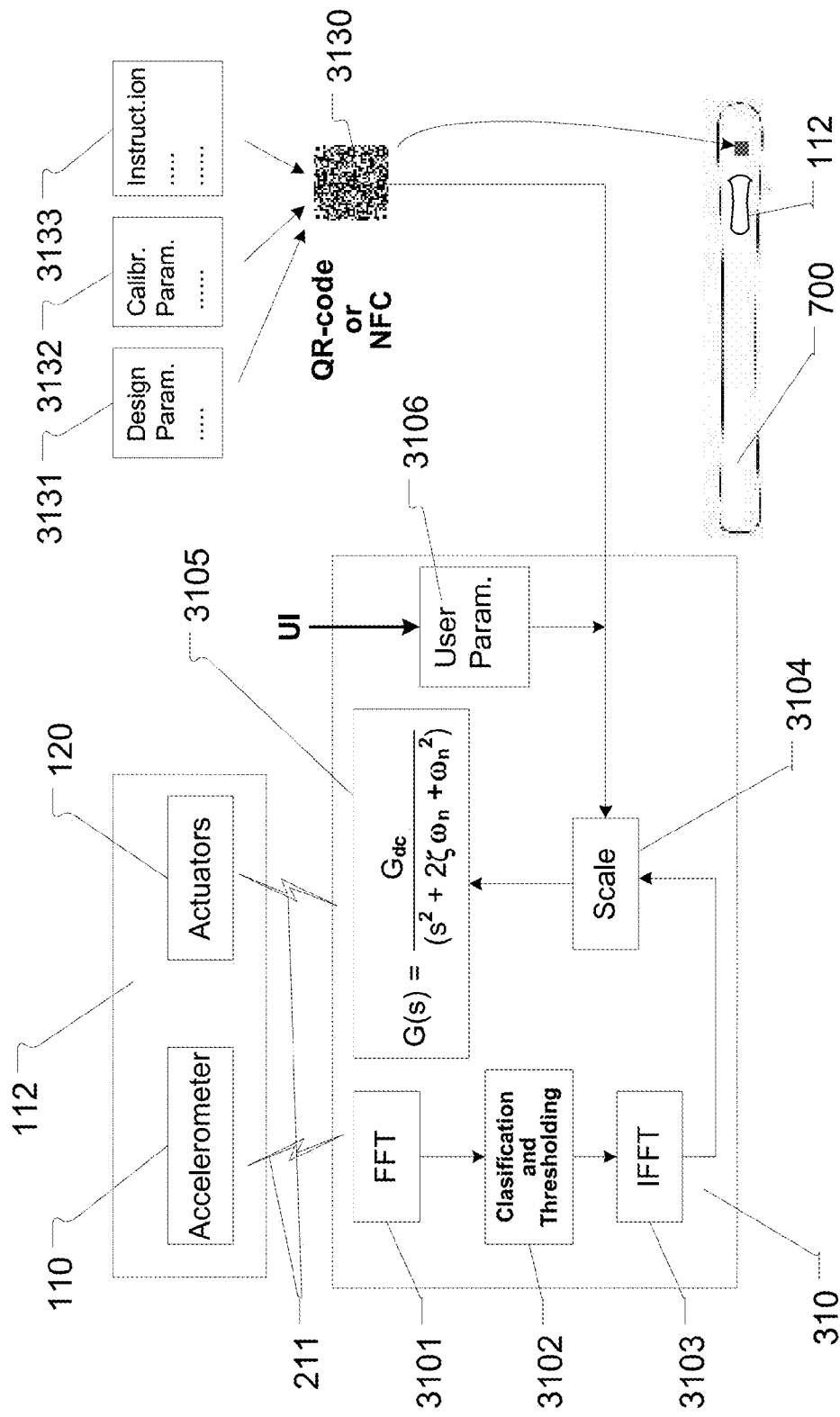
FIG. 13 illustrates the functionality of the ski vibration control system.

Location, orientation, number of actuators and their dimensions may differ from the exemplary structure presented in FIG. 4, in order to provide optimum vibration control for different type of skis. An example of such differently designed actuator sub-system is presented in FIG. 12, while FIG. 13 presents yet another embodiment of the vibration control actuator sub-system 112, integrated into the core of the ski while the control and the Bluetooth radio interface are encapsulated and attached to the top surface of the ski.

Figure 14:
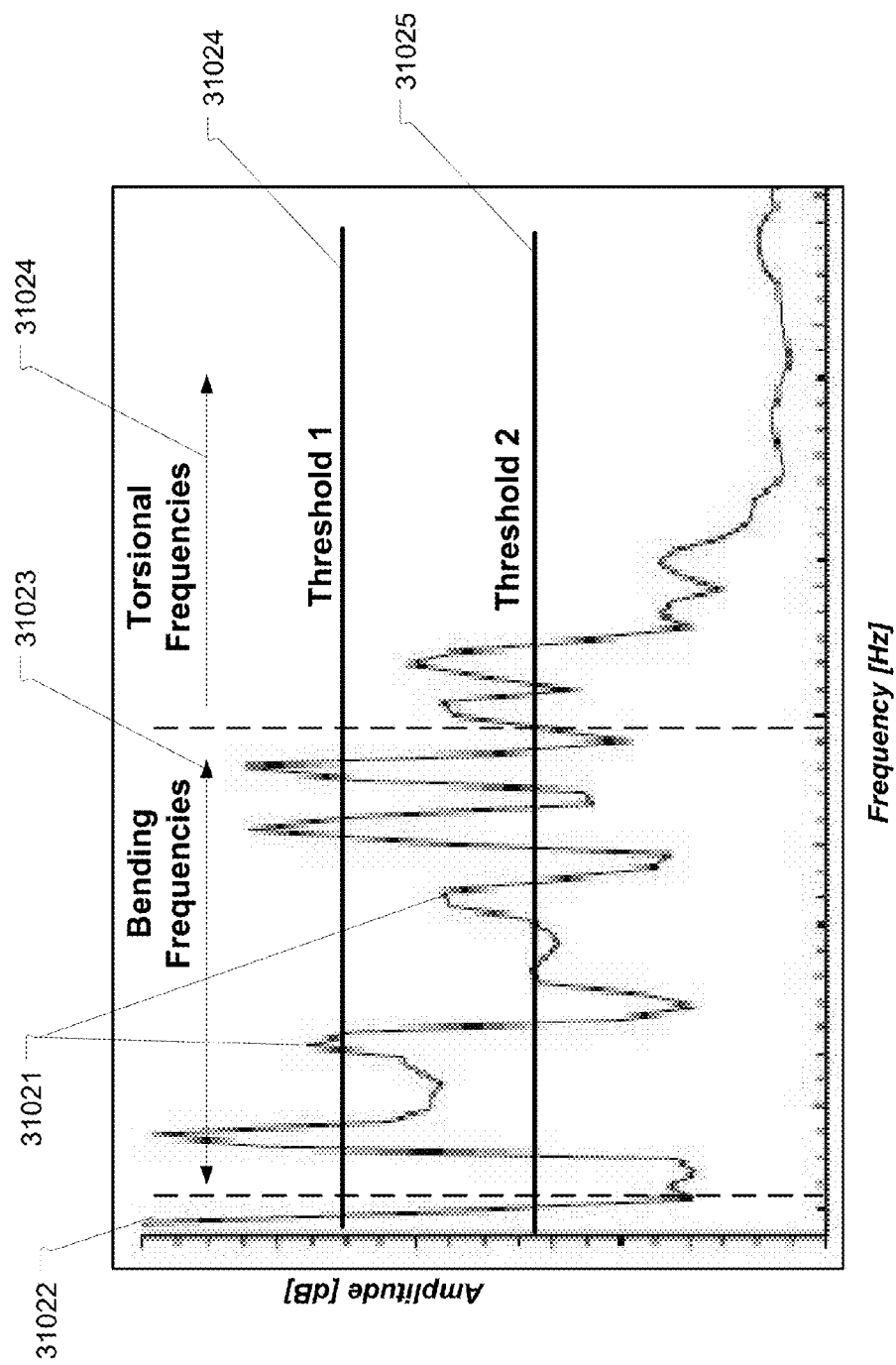
FIG. 14 illustrates analytical thresholds used to classify ski vibration, such as: vibration frequencies and amplitudes, classification and thresholding.

The robust, chevron stale (bent-beam) thermo-electric MEMS actuator 120 offering large design and fabrication flexibility is presented in FIG. 14. The desired performance (force), displacement distance, etc. can be achieved by stacking an appropriate number of V shaped "legs" and selecting "leg" length, cross-section area, and offset. Actuator enclosure 1201 is constructed in such a way that the side walls of the enclosure allow for some expansion, for example 1-2 mm, while the front and rear sides of the enclosure are from a rigid material, such as aluminum alloy to transfer the force of the expanding actuator to the displacement cores.

The control signal for such thermo-electrical actuator is applied to the anchor terminal pad 1202, permanently attached to the end wall of the actuator enclosure, heats the beams of the stacked actuators 1203 providing thermal expansion caused through the Joule heating of the beams Such expansion is transferred into displacement of the movable shuttle 1204. The force 1205 and the distance 1206, the movable shuttle is displaced due to the heating effect is proportional to the current and grows with the number of stacked actuator beams.

Figure 15:
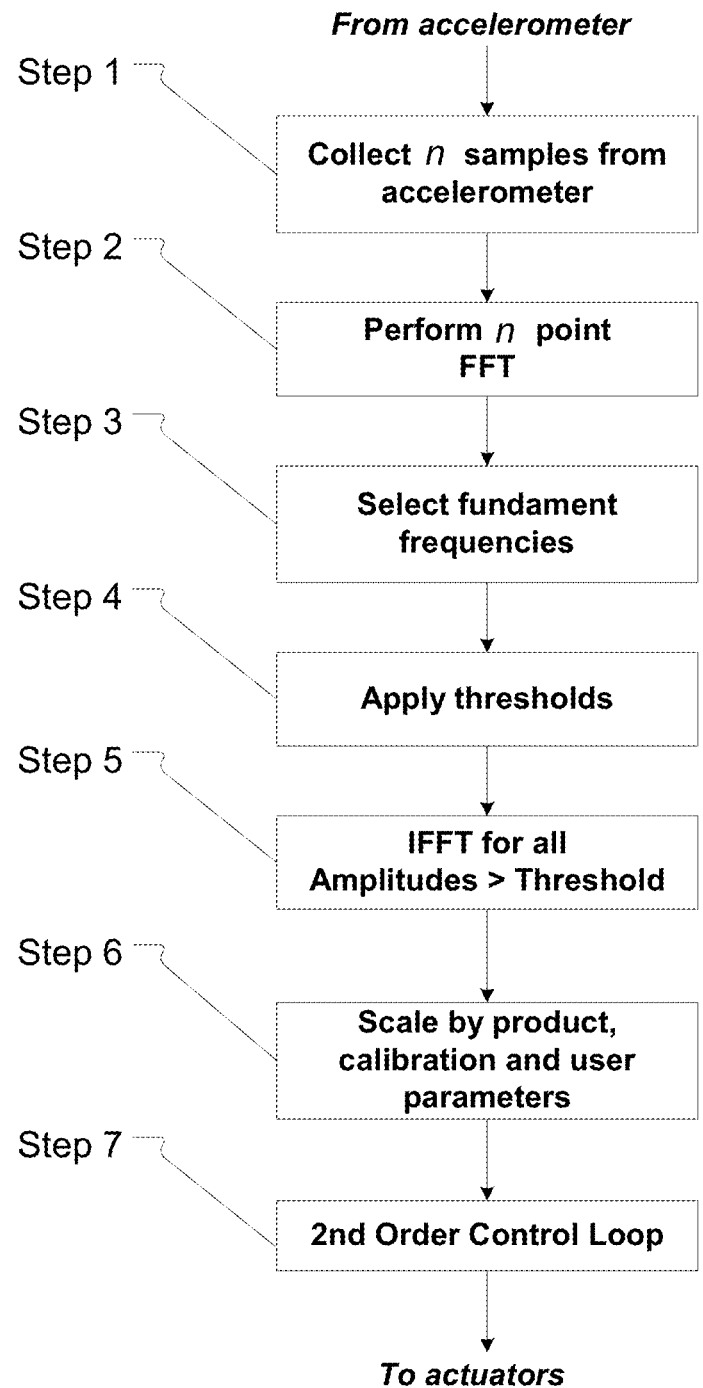
FIG. 15 illustrates the control flow of the ski vibration control system.

An example of such vibration control system is presented in FIG. 15. Here actuator sub-system 112, within ski 700 is in communication with the vibration analysis application 310 residing in the user smart-phone using PAN wireless interface (such as low power Bluetooth), 211. The analysis application receives samples of x/y/z vectors from the accelerometer embedded in the actuator sub-system at the rate suitable to determine ski vibration, where the x[n] sequence of samples represents continuous-time domain function x[t], at discrete moments in time t=nT, where T is the sampling interval in seconds, and $f_s=1/T$ is the sampling rate (samples per second).

Such sequence x[n] of length satisfying bandwidth of the vibration frequencies and the desired resolution is expressed as:

$$X_{2\pi}(\omega) = \sum_{n=-\infty}^{\infty} x[n]e^{-i\omega n}.$$

and after processing by the Discrete Fourier Transform (DFT) 3101, provides an approximation of the continuous Fourier transform function:

$$X(f) = \int_{-\infty}^{\infty} x(t) \cdot e^{-i2\pi ft} dt.$$

The power spectral density (PSD) of ski vibration is estimated and the results applied to the classification and thresholding function 3102.

This PSD (frequencies and amplitudes) of ski vibration is first classified in terms of fundamental and harmonic frequencies and is presented in FIG. 16. Such classification can be performed using multi-taper spectral estimator utilizing several different orthogonal data tapers, or any other suitable technique well known to those skilled in art. In effect of such classification, all harmonic frequencies, 3021 of the fundamental frequencies between 5 Hz and 200 Hz are discarded. Then the remaining fundamental frequencies are classified into three separate categories: natural frequencies 3022; bending frequencies 3023; and torsional frequencies 3024. Then, the bending and the torsional frequencies amplitudes are compared to their respective thresholds: 3025 and 3026. All amplitudes below the respective thresholds are discarded while frequencies and amplitudes for bending frequencies and frequencies and amplitudes for torsional frequencies are added to produce composite matrix of the residual distractive vibration at time $\Sigma X'_f[t]$.

Classification for bending and torsional frequencies is used to distribute the dampening force according to the type of vibration—along the ski logitudal axis for all bending vibration, and along the perpendicular ski axis (or combination of logitudal/perpendicular) axis for the torsional vibrations, while the natural bending frequencies attributed to ski construction materials and intended to provide flexibility and the desired ski response are discarded.

Next, the composite residual vibration matrix is applied to the Inverse Discrete Fourier Transform (IDFT), function 3103, producing time domain representation of the residual vibration signal. Such signal, is normalized in function 3104, before it's applied to the 2$^{nd}$ order control function 805, of a general form $G(s)=G_{dc}/(s^2+2\zeta\omega_n+\omega_n^2)$, and finally at time t+Loop_Delay as a control signal to the actuators.

Before this time domain representation of the residual vibration is presented to the 2$^{nd}$ order control loop 3105, the vibration response signal from the ski is normalized by the ski specification and calibration parameters 3120, and the user physical parameters 3106, to obtain the desired control ratio $\zeta$. This is achieved by scaling the residual vibration at function $\Sigma X'_f[t]$ by ski design and calibration parameters and the user current set-up of "target ski response" parameter.

The first information 3131, contains such information as: ski length, width, weight, deflection to standard loads, etc. The second information 3132, contains data obtained during post-manufacturing calibration process of each individual ski, and contains such information as: vibration damping function $Xe^{-\zeta\omega_n t}$. The third information contains user physical characteristic with such information as: user weight, height, expertise level, etc. In addition, the third information may contain current "target" ski response characteristics, such as: current snow conditions—for example, soft, hard, icy, etc.; desired ski response—for example soft, stiff, etc. as well as the user contact list, which may contain emergency contacts—used by the application to send SMS messages if emergency is detected, and/or list of IP destination to which ski response data may be send.

The ski design 3131, calibration 3132, information and the precoded messages 3133, is entered to the application memory by scanning of the QR-code or NFC tag attached to the ski. The user related information is usually entered through the smart-phone user interface (UI), or downloaded from a remote location using cellular network radio interface. Information 3133, among others may contain: operational instructions; time or event or time triggered messages; event triggered advertisement—for example, after run, on the ski lift, etc. Such precoded information may be in textual or audio/visual form.

Parameters contained in information 3130 and the user specific information is used to calculate the final value of the damping coefficient $\zeta$, does "tuning" user ski to the current snow conditions or the desired type of run, for example: recreational vs. race. Such functionality is enabled by "scaling" the actuators force (displacement) does effecting the amplitude of response to the bending forces. The effect of such controlled dampening is presented in FIGS. 9B and 9C.

Information 3131 (ski length, width, weight, etc.), is directly obtained from the ski design parameters—such as ski type, materials, etc., while information 3132, is obtained during ski post-manufacturing calibration process. Such calibration is necessary as the exact characteristics of each individual ski (flexibility, displacement due to bending forces, resonance vibration, etc.), may differ and are unknown a priori. Such ski calibration process is presented in FIG. 17 and described below in details—to obtain unbiased calibration data (ski, not the response of vibration control system), vibration control system must remain inactive.

In Step 1, the deflection of the ski 700, in response to natural bending forces as described in relation to FIG. 9A is measured. Here the ski is placed in the supporting mechanism 730, with supports located in the middle points between center of the ski effective length, and both ends (front and rear), of the ski effective length. Then a load 740, of force $N_k$ is applied to the center point of the ski effective length and the displacement (representing ski flexibility), is recorded and stored in the calibration table. The load value may be changed to obtain more then one result.

Figure 9B:
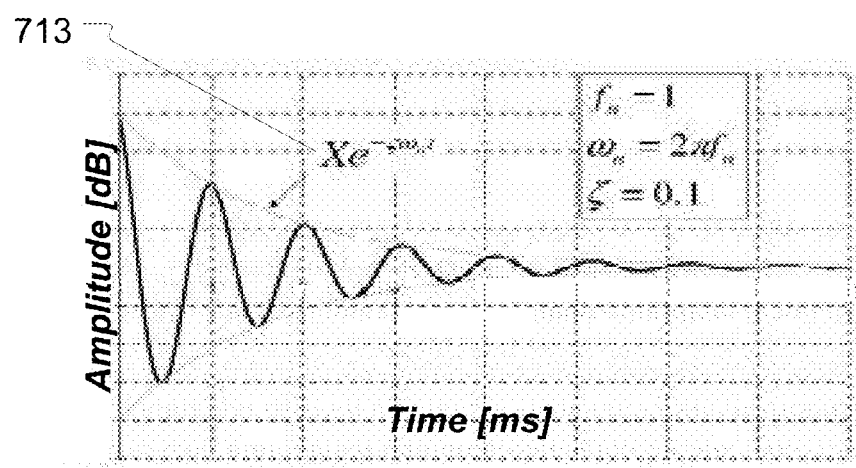
FIG. 9B is a time domain representation of vibration of the "soft" ski.
Figure 9C:
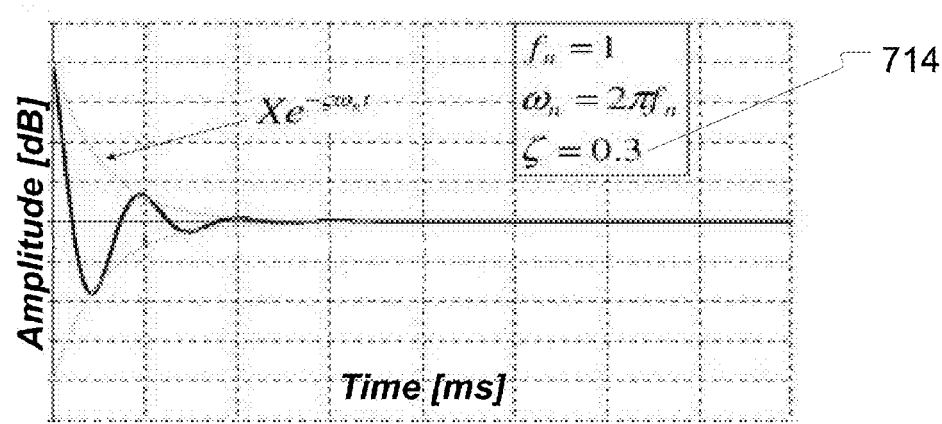
FIG. 9C is a time domain representation of vibration of the "stiff" ski

In Step 2, the load 740, is removed after application and the ski is left to vibrate in response to such force, while the decaying function $Xe^{-\varsigma\omega_n t}$, of FIG. 9B, representing natural dampening characteristic of the ski is recorded and stored in the calibration table.

Next, the support structure 730, is placed between the center of the ski effective length and the front end of the ski effective length and the procedures described in Step 1 and Step 2 of is repeated, at which point, the ski calibration table is populated with the ski flexibility and vibration dampening parameters.

Operation of vibration control system is presented in FIG. 11. Here in Step 1, n samples of x/y/z coordinates received from the actuator sub-system accelerometer are accumulated. Then in Step 2, an n point DFT transform $$X(k) = \sum_{n=0}^{N-1} x(n) e^{-j\frac{2\pi k n}{N}} \quad k = 0, 1, \ldots, N-1$$

is performed resulting in approximation of the ski vibrations, represented by the matrix:

$$F = \begin{bmatrix} \omega_N^{0 \cdot 0} & \omega_N^{0 \cdot 1} & \cdots & \omega_N^{0 \cdot (N-1)} \\ \omega_N^{1 \cdot 0} & \omega_N^{1 \cdot 1} & \cdots & \omega_N^{1 \cdot (N-1)} \\ \vdots & \vdots & \ddots & \vdots \\ \omega_N^{(N-1) \cdot 0} & \omega_N^{(N-1) \cdot 1} & \cdots & \omega_N^{(N-1) \cdot (N-1)} \end{bmatrix}$$

where:

$\omega_N = e^{-2\pi i / N}$.

Classification of vibrations as presented in FIG. 16 is performed during Step 3 and Step 4. In Step 3, harmonics frequencies 31021 are discarded, while the fundamental frequencies are retained. Then in Step 4, natural bending frequencies 31022, which are attributed to the ski design parameters and intended to provide desired flexibility and stiffness are separated, from bending frequencies 31023, and torsional frequencies 31024. Then a first threshold 31025, is applied to frequencies in the bending frequency bin 31023, and all frequencies with amplitudes above such threshold are retained. Consequently, second threshold 31026, is applied to frequencies in the torsional frequency bin 31024, and frequencies with amplitudes above such threshold are retained while those below discarded.

Such classification and selection is necessary for the following reasons: a), bending vibrations, which occur at a lower frequency range and cause ski to vibrate along it's logitudal axis, have higher amplitude; b) torsional frequencies, having lower amplitudes are more destructive as they cause side-to-side vibration of the ski; c) application of dampening stimulus to the fundamental vibration frequency, also effects harmonics of this frequency; d) selecting an appropriate threshold levels increases system performance by making it more resilient to noise, while lowering the processing requirements and power consumption; e) if actuator configuration allows (FIG. 5), applying control signal to certain actuators or in certain order, provides ability to attenuate both types of vibrations independently. Furthermore, attenuating only vibration above certain thresholds enhances comfort without degradation of enjoyment of interaction between ski and snow.

In Step 5, the resulting matrix is applied to the Inverse Discreet Transform (IDFT) 3103, does producing time domain representation of the residual ski vibration signal. Such inverse transform can be obtained by inverting the resulting frequency matrix $$F^{-1} = \frac{1}{N} F^*.$$

In Step 6, signal representing frequencies and amplitudes of vibrations selected for dampening, is normalized (scaled), by the ski design 3131, calibration 3132, and user parameters 3106, to produce the desired control ratio coefficient $\zeta$. This may be achieved by employing one of the suitable techniques well known to those skilled in art, such as: Least-Squares Estimation, Discrete Optimal Estimation, or by simple scaling the measured response signal by the "reference" signal derived from calibration parameters and user set-point parameters. The coefficient $\zeta$ controls the gain of damping function $Xe^{-\varsigma\omega_n t}$.

In Step 7, control signal $G(s) = G_{dc}/(s^2 + 2\zeta\omega_n + \omega_n^2)$, is generated and send to the actuator sub-system over the smart-phone Bluetooth radio interface 211.

It has to be noted that step 6 and step 7 may be implemented as a well known PID (Proportional-Integral-Derivative), controller of the form:

$$u(t) = MV(t) = K_p e(t) + K_i \int_0^t e(\tau) d\tau + K_d \frac{d}{dt} e(t)$$

Such controller may be implemented in an appropriate to the particular smart-phone programming language, such as: C, C++, or Java. An exemplary C code of a PID controller follows:

```
/* memories */
float S = 0.0, J = 0.0;
void dispid cycle ( ) {
    float I,O;
    float J,1,S,1;
    I = Input( );
    J__1 = I;
    S__1 = S + 0.1 * I * 4;
    O = I * 5.8 + S__1 + 10.0 * 3.8 * (I-J);
    J = J__1;
    S =S__1;
    Output(O);
}.
```

Wireless Network for Monitoring and Analysis of Skiing

The monitoring systems described in the previous sections requires approximately 20 MEMS accelerometers and actuators. When tails ski vibration control sub-system or even more advanced system controlling the ski edges is added, the number of sensors/actuator may easily reach several dozens.

The fundamental requirements for the wireless network providing short range communication with sensors and actuators embedded in the ski equipment and the smart-phone installed monitoring and analysis application are: a) compatibility with smart-phone radio interfaces; b) reliability; and c) ability to access multiplicity of devices with latency required to satisfy the control environment.

While the common smart-phone Bluetooth radio interface satisfies first and second requirement and can operate in the networks containing hundreds or more Bluetooth enabled devices, the fundamental characteristics of Bluetooth specification allows only eight devices (master and seven slaves) share the same "layer" of connectivity. This type of connectivity is frequently referred as a pico-net and is presented in FIG. 16A. Bluetooth architecture allows connection of more devices by allowing some of the devices to be shared with another pico-net. Such device may be a slave of both pico-nets or a slave in one pico-net and master in another pico-net and the topology of such networks are presented in FIG. 16B, and commonly referred as a two-hop or multi-hop pico-net.

While the advantages of multi-hop pico-nets are obvious—ability to access multiplicity of devices, the disadvantage is also clear—latency increases proportional to number of "hops" and the number of connected devices. This is due to the fact that Bluetooth Physical Layer operates in a TDD (Time Domain Division) mode with slot period of 625 µs, where the even numbered slots are used for transmission from master to the slave(s), and the add numbered slot are used for transmission from the slave(s) the master. In such transmission protocol, slave addressed (pooled) in slot 1 responds in slot 2—so two consecutive slots are required to service single slave device. Such two consecutive slots are frequently referred as "Bluetooth frame". As such the minimum latency (single slave) of Bluetooth network is equal to 1.25 ms. When several slaves are present and the Round-Robin schedule method is used the period to servicing the same slave (latency of the system) is $2*N*626$ µs, where $N\leq7$, is the number of slaves, and frequently referred as 'Bluetooth meta-frame". For pico-cell with seven slaves such mete-frame (and latency of the control loop), is equal $2*7*625=8.75$ ms, defined in FIG. 16A as $\Delta T1$.

However, in the typical control system an additional processing time is required between input data sample and the output data sample. If for a single-hop pico-net, the latency equals to $2*N*625$ µs, then network with seven slaves has latency of 8.75 ms, while network consisting a smart-phone based master and 30 devices (combination of sensors and actuators), would have latency of 37.5 ms, or apx. 26.6 Hz—clearly not acceptable for the ski control application.

Figure 16A:
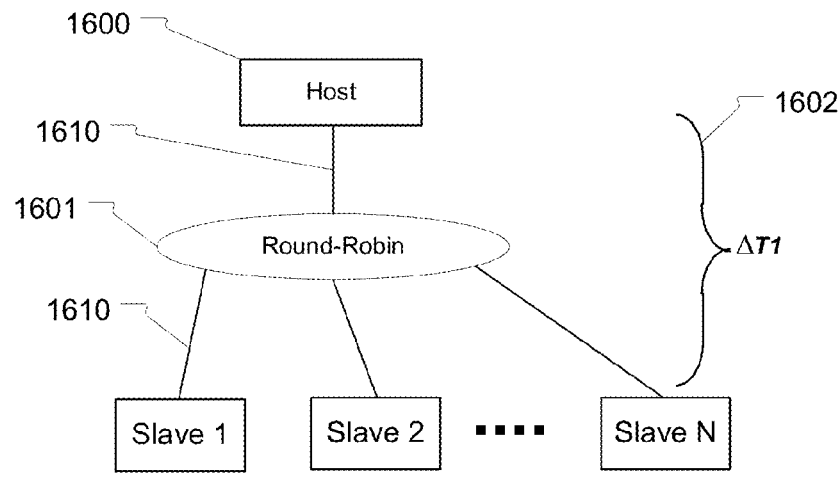
FIG. 16A illustrate topology and delays of a typical wireless single-hop pico-net.
Figure 16B:
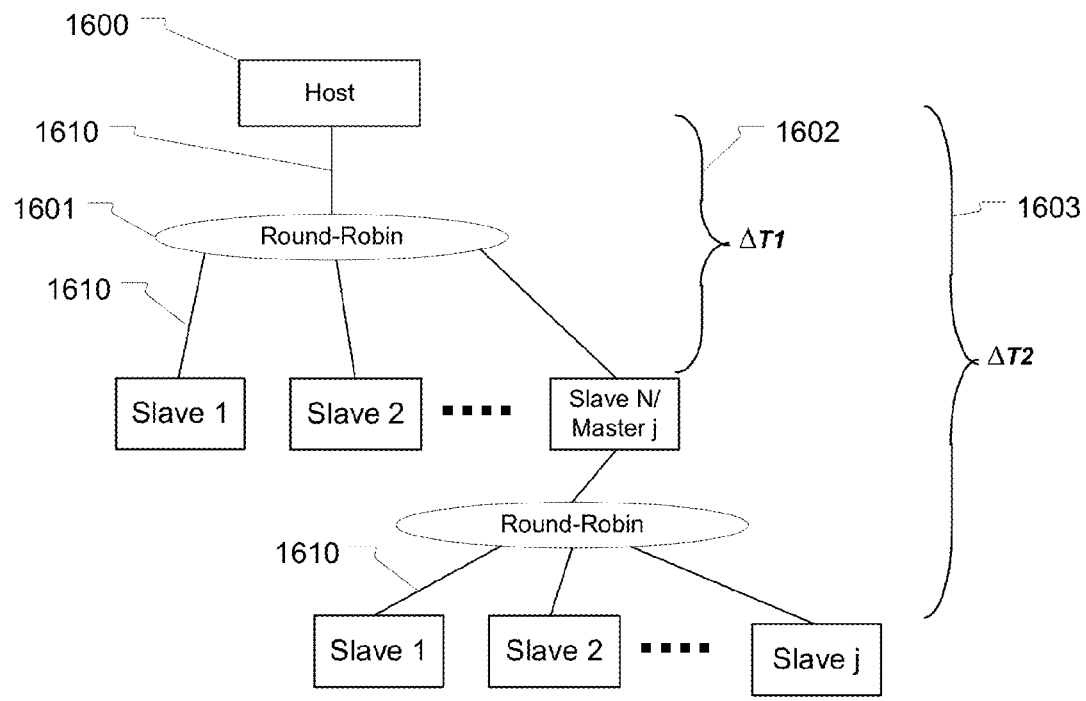
FIG. 16B, illustrates topology and delays of multi-hop pico-net topology when one slave provides a bridge (master) function to second layer of slaves.
Figure 17:
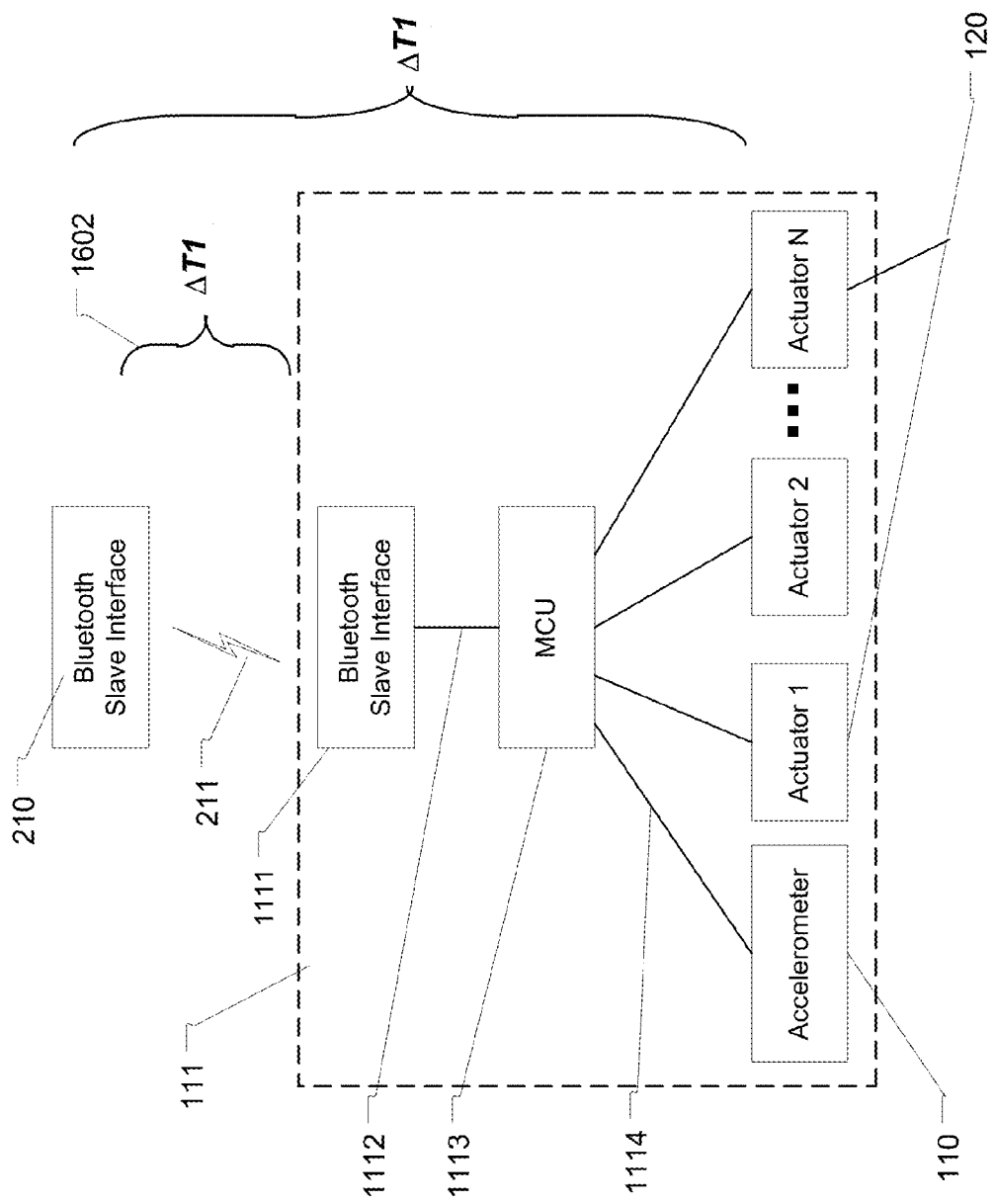
FIG. 17 presents a hierarchy of a single-hop wireless heterogeneous pico-net consisting a Bluetooth master and the actuators sub-system slave consisting multiplicity of devices communicating with the Bluetooth slave using digital wired interface.
Figure 18:
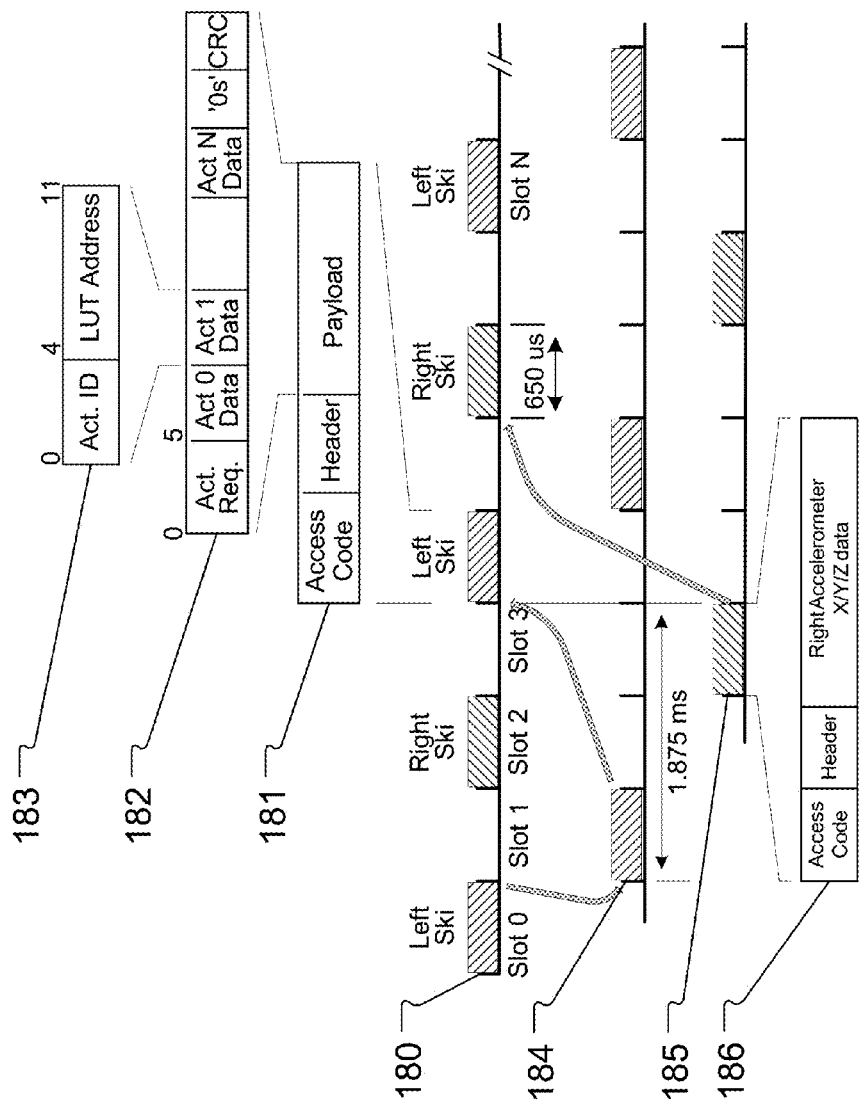
FIG. 18 presents communication protocol of the single-hop communication network of the present invention.

The additive nature of the multi-hop network on the latency is presented in FIG. 16B. Here the host 1600, communicating with the slaves using Round-Robin scheduling algorithm 1601 over Bluetooth RF interface 1610, where the latency of the first layer (hop) of the network is $\Delta T1$. As the total number of slaves in this network exceeds 7, device N performs a bridging function (slave in one network and master in the other) to the second layer of network hierarchy. As such, the latency of such network will be $(2*N*625)+2*j*625)$, and is defined here as $\Delta T2$, the combined latency of first and second layer.

Consider that time difference in skiing competition is measured in 0.01 sec (10 ms), during which time forces experienced by skier body and ski/snow interface may change significantly many times, while the ski may vibrate at rate of 150 Hz, and to provide safety, time force is applied to skier knee which exceeds the safety criteria is measured in milliseconds—we realize a new network topology connecting sensors and monitoring application is required.

To address those issues we propose a novel network topology, which provides all benefits of Bluetooth radio interface (ubiquitous presence in smart-phones, easy to use, security, etc.), while providing benefit of connecting multiplicity of sensors and actuators embedded into ski equipment with the latency of a single-hop network. Furthermore, the Round-Robin scheduling scheme is supplemented with gating-off (no transmission), the RF transmission by the addressed slave, if such slave has no data to send, resulting in lowering slave's power requirements (extending battery life), and lower interference. Such scheme, is possible due to the fixed schedule associated with the Round-Robin access method and indicates that non-transmitting slave's current sample data are equal to the previous sample data.

The description of said wireless control network is presented in following sections and is based on the examples presented in this specification—namely: the ski vibration control system and skiing monitoring and analysis system. Specifically, it is based on network providing communication with the actuator sub-system presented if FIG. 11, consisting of one accelerometer and four sets of independently controlled actuators, and on the skiing analysis network presented in FIG. 5, consisting of 10 accelerometers attached to various of the skier. However, those skilled in art must find easy to expand said architecture with additional functionality, such as: additional actuators, control of adaptive ski bindings, etc.

This proposed topology is based on a heterogeneous network (wireless/wire), consists of one master device (smart-phone), and two actuator subsystems (left/right ski) consisting of an accelerometers and four actuators, for the total eleven devices in the network. The network is organized in such a way that also it consists of 10 slave devices, the master communicates directly with only two (one per ski), and the topology for ½ of this network is presented in FIG. 17.

Here the master 210, communicates with slave 141, over Bluetooth RF interface 211. The latency 1602, of this network is equal to $\Delta T1$ ($2*625$ µs), as the master communicate directly only with the Bluetooth slave interface 1111, but not with any other devices located inside the actuator sub-system. Instead the micro-controller (MCU) 1113, which controls the Bluetooth RF interface 1111 using digital bus interface 1112 communicates with the accelerometer and actuators using an appropriate digital interface 1114. As such, the latency of such network will be upper bounded by the delay of the Bluetooth frame $\Delta T1$, as the delays of the internal (to the actuator sub-system) digital interfaces are negligible.

Such architecture is enabled by communication protocol in which a multiple devices can be addressed within a single Bluetooth slot and independent of number of devices located within the sub-system. The timing diagram of communication protocol for such network topology (actuator sub-system) is presented in FIG. 18, and described in details in the following paragraphs.

The master schedules the left/right ski actuator subsystem in a traditional Round-Robin fashion, addressing the left actuator sub-system in slot 0 and right in slot 2, etc. The control packet 180, transmitted by master consist of the device access code 181, (address of left/right ski), the packet header (packet number), and the control packet payload 182, is sent in response to contains the address of the slave 181, a header of the packet, and the control packet payload consist: an accelerometer control record containing the request for new samples from accelerometers identified by the accelerometer ID (substituting for traditional Bluetooth pooling), and a multiplicity of actuator control records 183. Each of the actuator data record consists of actuator address identifier and the actuator control data. The actuator control record is repeated for each of the multiple actuators embedded in the actuator sub-system, and the control packet payload is padded with '0s' bits to adjust it's size to the Bluetooth packet size, before such Bluetooth packet is encoded using forward error correction code (FEC).

In response to packet 181, in slot 1, the sub-net slave located in the left ski actuator sub-system sends data packet 186, which contains actuator samples record(s) from the left ski accelerometer 110, sampled by the MCU at the Nayquist rate of the highest frequency the system is designed for. Said samples may filtered and/or interpolate before are sent to the Bluetooth slave interface for transmission to the master. When change between the previous sample and the current sample is smaller then predefined, the MCU may instruct the slave Bluetooth interface to "gate-off" it's transmitter does reducing the slave power consumption and extending accelerometer sub-system battery life. When the master, detects "gated-off" slot, it will recognize this lack of transmission as "no-change" and appropriately update the analysis system, which may farther filter results.

In such system, the total delay between the request for accelerometer sample and the actuator feedback command (control packet), is $\Delta T1$ or 1,875 ms and the bandwidth of the control system is apx. 530 Hz, well above the requirements of ski analysis system.

The control signals sent to the actuators are the time domain representation of the inverse of the ski residual vibration signal, normalized by the ski and skier parameters and applied to the control loop of form of $G(s)=G_{dc}/(s^2+2\zeta\omega_n+\omega_n^2)$. To lower bandwidth and power requirements, rather then sending the actual results of such function to the actuators, only eight bit pointer to the look up table (LUT) located in the actuator sub-system MCU is send—this method is presented in FIG. 19. The effect—short slot and transmission time, and consequently low duty cycle of slave Bluetooth transceiver—see FIG. 20.

Figure 19:
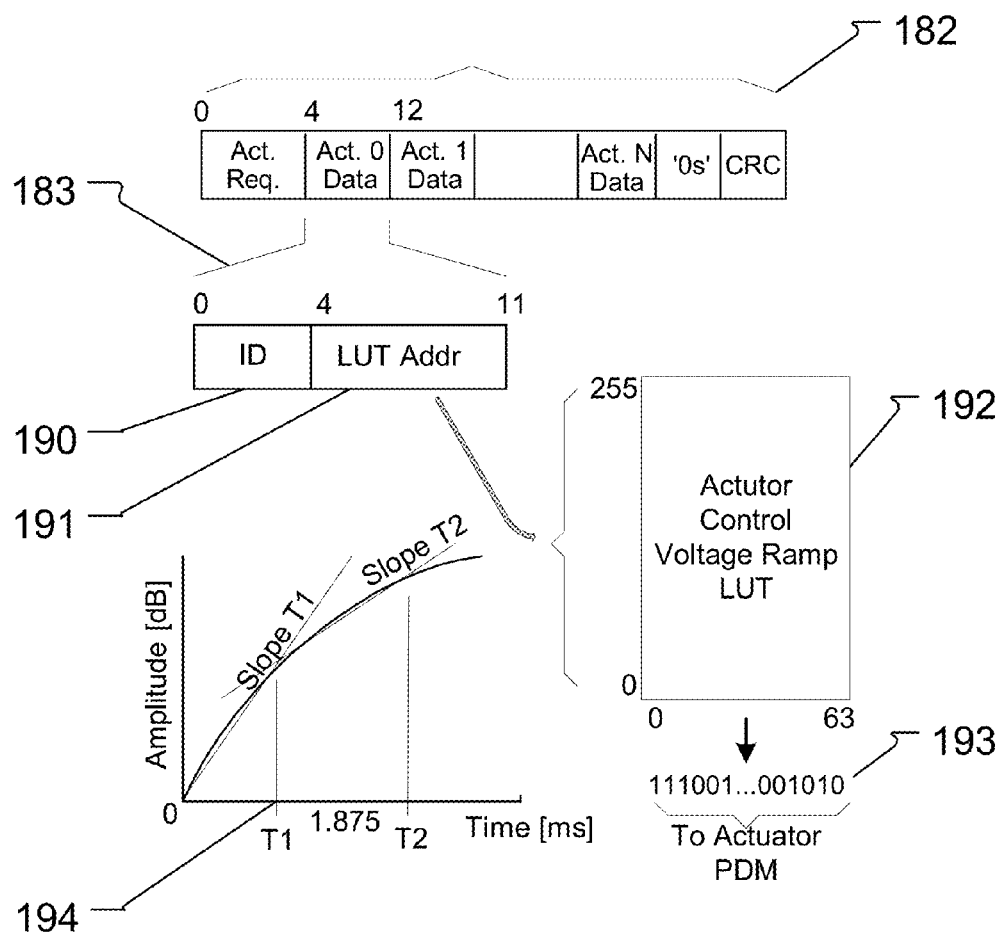
FIG. 19 presents the actuator sub-system control field and the method of addressing and controlling of a single actuator.
Figure 20:
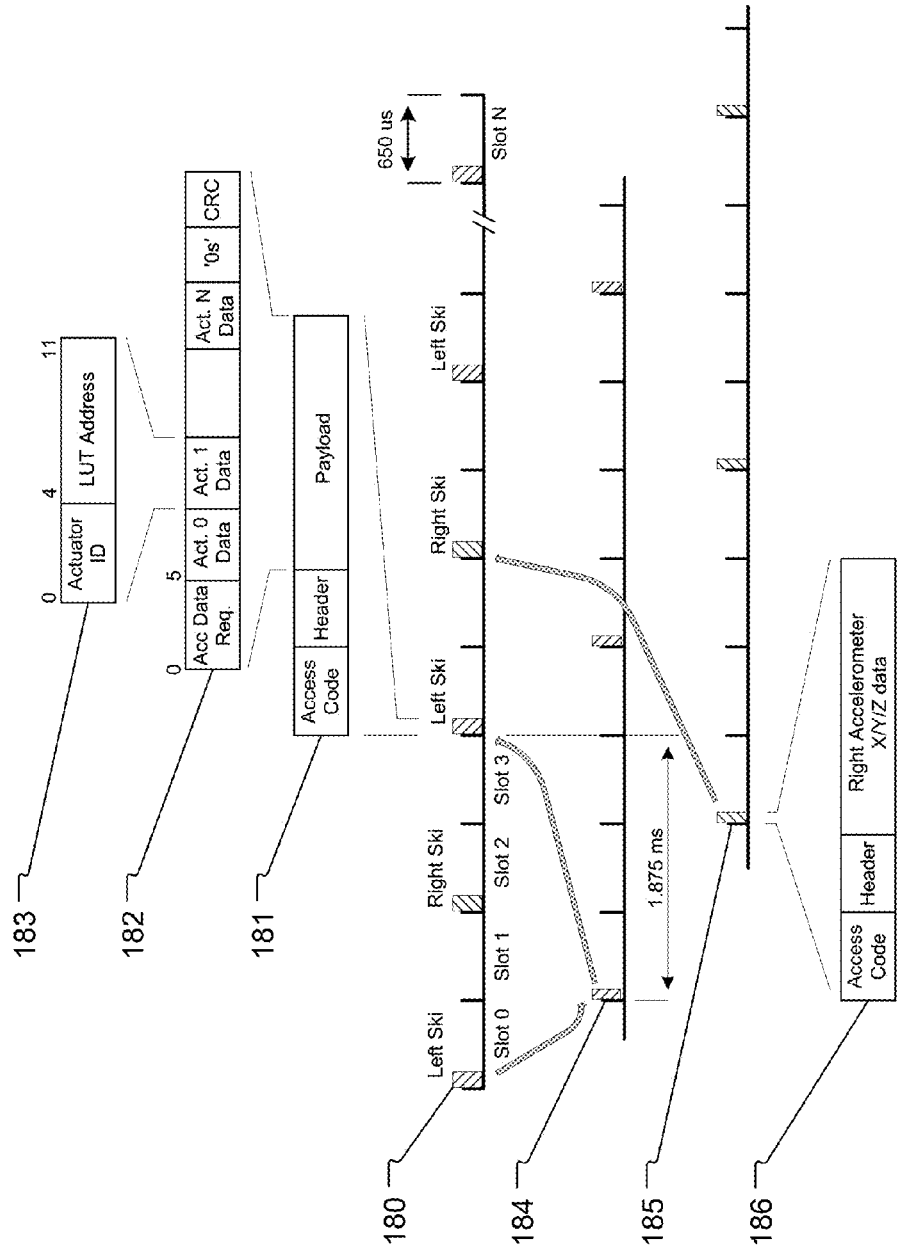
FIG. 20 presents the communication protocol duty cycle and content of the control fields.

The method of constructing the actuator control record is described in FIG. 19. The control record 183 consists of the actuator ID 190 (address of the actuator within the actuator sub-system), and the actuator control word, in form of a pointer (address) 191, to the LUT 192, containing the control word 193, which is applied to the actuator, and representing a Mean Squared Error of the piece-wise fit between the optimal control signal and the closest impulse response stored in the LUT. Each location of the LUT is of length N, and represents a specific impulse response in form of "1s" and "0s", where the density of "1s" define the slope (time response/frequency), of the dampening signal and the total number of "1s" defines the amplitude of the dampening signal at time 194. This LUT is arranged as an array of 256×N, where the N depends on the control period cycle, the desired resolution and the maximum amplitude of the dampening signal. Such LUT is stored in the MCU 1113, non-volatile part of memory. The LUT output pattern of "1s" and "0s", may be directly applied to the pulse density modulated (PDM), digital-to-analog converter to generate the desired control voltage for the actuator.

Figure 21:
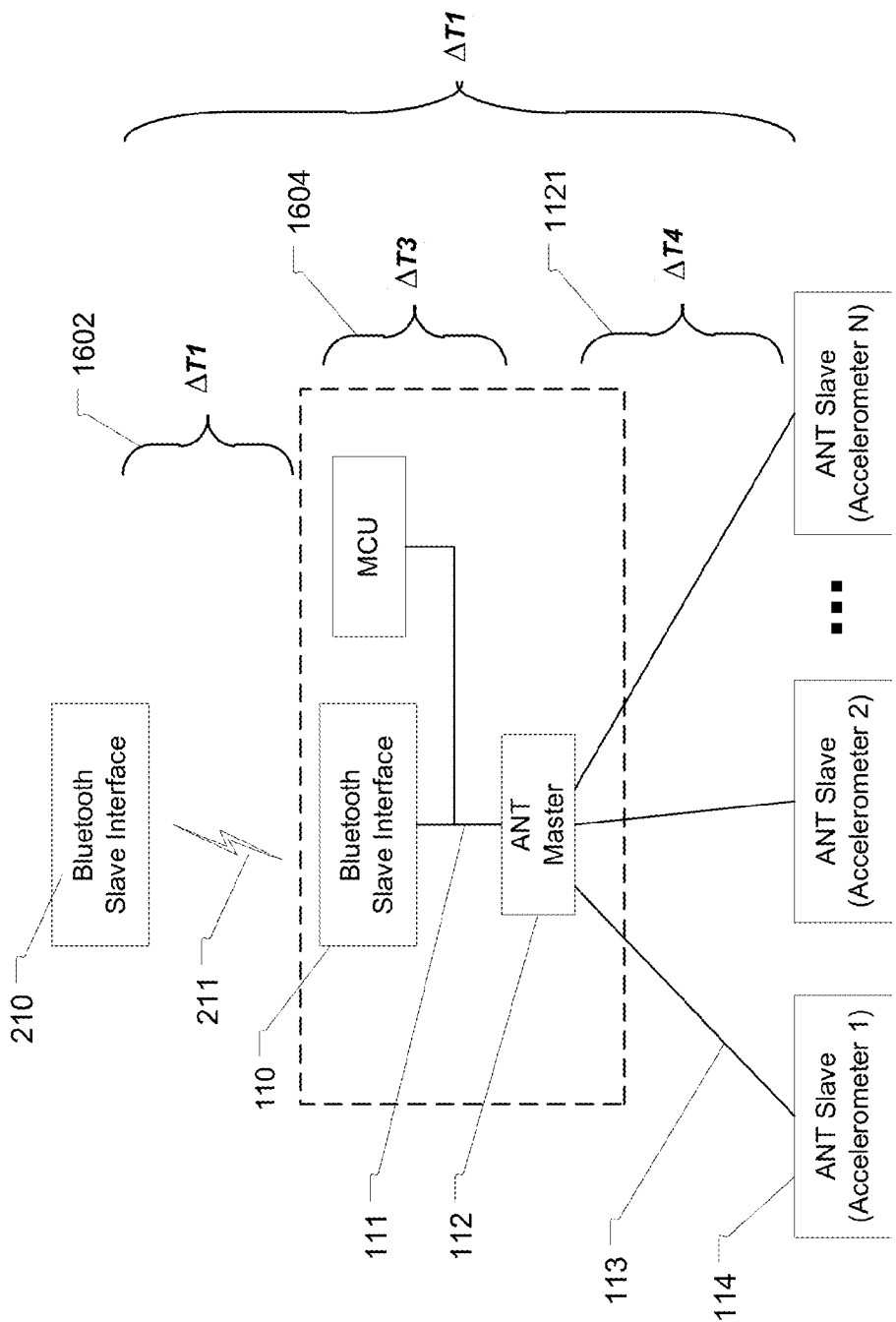
FIG. 21 presents a hierarchy of wireless heterogeneous pico-net consisting a Bluetooth master and the sensor sub-system slave communicating with a multiplicity of devices using ANT wireless personal access network.

A similar concept of fully wireless heterogeneous control network may be deployed to communicate with the skiing analysis application presented in FIGS. 2 through 5. Such system consists of a multi-axis accelerometers embedded in the skier clothing, and may consist of eight or more accelerometers. From FIG. 5, one may conclude that topology presented in FIG. 17, require embedding some sort of digital bus into the ski clothing—in most cases very undesirable, or to deploy topology of FIG. 16B (more then seven slaves), which would have an unacceptable latency, specifically in case the ski vibration control system and/or ski binding system is also deployed. Topology of a wireless heterogonous network suitable for such control network is presented in FIG. 21.

In such network there is only single sub-bet slave communicating with the smart-phone based master. This Bluetooth slave may also act as master for the ANT wireless network, does providing the benefits of wireless communication and low latency (short slot time). Here the Bluetooth slave device consist also ANT master device (or communicates directly with the ANT master device or both the Bluetooth slave and ANT master are under direct control of local MCU), and the ANT master communicates with the ANT slave devices organized as star network. Each ANT slave transmits data from single accelerometer to the ANT master. In such a way, during each Bluetooth frame, the master 210, pools the sub-net slave requesting new samples received by the ANT master from all ANT slaves, obtained form accelerometers. The latency of this network is defined by the latency of $\Delta T1+\Delta T3+\Delta T4$. As previously discussed $\Delta T3$ is the internal delay of digital network and as such negligible, while $\Delta T4$ equals the number of ANT slaves N*150 μs, so for the network of eight accelerometers $\Delta T4$ is 1.2 ms, and in effect the latency of such network is equal to $\Delta T1$. One must remember that since ANT network is not synchronized with the Bluetooth time slots, the ANT may accessed immediately after Bluetooth slave detects the pooling request. For the mix network (vibration control+skiing analysis), the latency of the analysis network is again $\Delta T1*N$ as the $\Delta T4$ is "hidden" by the latency of network scheduling algorithm.

Figure 22:
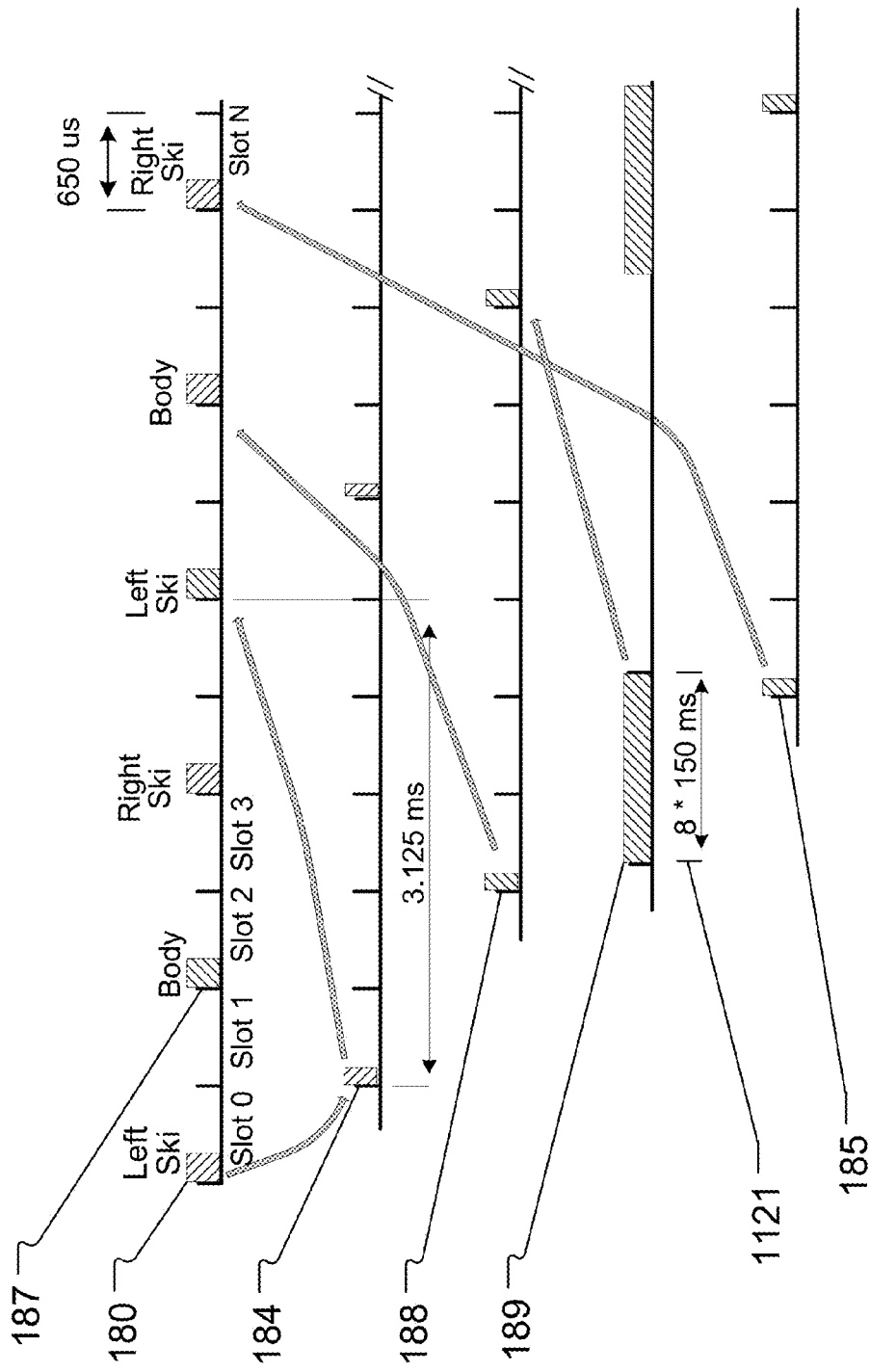
FIG. 22 presents the communication protocol and timing diagram of the single-hop network consisting of two heterogeneous networks of the present invention.
Figure 23:
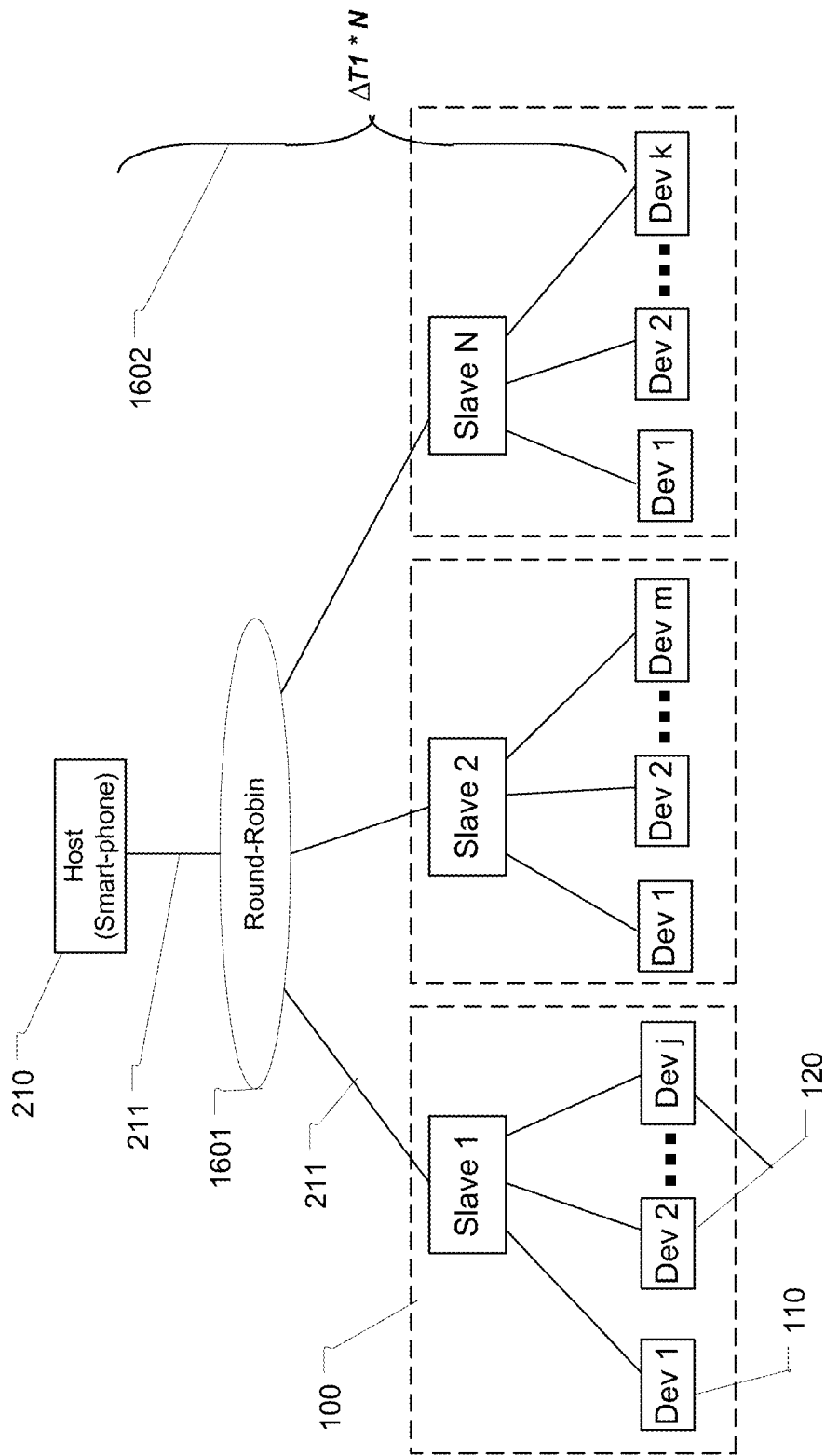
FIG. 23 presents an exemplary topology of the wireless network consisting of multiplicity of actuators and sensors while satisfying the requirements of single-hop architecture.

The timing relation of such mixed (ski vibration control+ ski analysis control), network is presented in FIG. 22. Here skiing analysis slave 186 (designated as "body"), transmission is in slot number 2, and the scheduler Round-Robin cycles "left-body-right", so: in slot '0' control packet containing accelerometer control record (request for data from accelerometers), and the actuator control record (control signals for actuators), is sent to left ski "sub-system"; in slot '2' control packet—containing accelerometer control record (request for accelerometer data from all accelerometers within the ANT body area network), and empty payload is sent to the "body sub-net" Bluetooth slave; and in slot '4' control packet—request for accelerometer data and the actuator control record is sent to right ski "sub-system". While the samples from the left ski accelerometer is transmitted in slot '1', the samples from all eight accelerometers is within the "body sub-net" are transmitted in slot '3', and samples from left ski accelerometer is transmitted in slot '5'. The latency 1121 ($\Delta T4$), of this body area network consisting eight accelerometers is only 1.2 ms, less then 1.25 ms Bluetooth frame, does allowing up to 24 ANT/accelerometer slaves to operate with the latency penalty equal to $\Delta T1$. Such heterogeneous (wireless/wire or wireless/wireless), network topology may be extended to provide support for another layer of sensors and/or actuators—for example ski bindings sensor/actuator sub-system, or another ski actuator sub-system at negligible degradation to the overall performance of the system. This extended network topology is presented in FIG. 23, indicating that the network latency is upper bounded only by the number of slaves in the $1^{st}$ layer of the hierarch for a number of slaves equal seven or less.

Although the embodiments above have been described in considerable detail, numerous variations and modifications will become apparent to those skilled in the art once the above disclosure is fully appreciated. It is intended that the following claims be interpreted to embrace all such variations and modifications.

I claim:

1. A wireless hierarchical heterogonous network providing communication between a smart-phone based analysis and control application and a multiplicity of sensors and actuators embedded in a ski equipment comprising:
  a first layer of the wireless hierarchical heterogeneous network composed of the smart-phone based Bluetooth master transceiver and up to seven Bluetooth slave transceivers embedded in the ski equipment;
  a second layer of the wireless hierarchical heterogeneous network composed of up to seven network sub-nets, each comprising multiplicity of Microelectromechanical Systems (MEMS), sensors and actuators;
and wherein the master of the first layer of the wireless hierarchical heterogeneous network using a Round-Robin scheduling scheme sends to each slave of the second layer of the wireless hierarchical heterogeneous network a control pocket comprising: an access code of the sub-net; a header of the packet consisting packet number; and the control packet payload comprising multiplicity of control records dedicated for each individual device within the sub-net; and wherein upon reception of said control packet, the slave responds with a packet data containing data samples obtained from sensors located within the sub-net.

2. The system of claim 1, wherein first layer of wireless hierarchical heterogeneous network is configured as a single master of a pico-net, in which each slave of the pico-net provides a single-hop bridge to all devices located within the pico-net.

3. The system of claim 1, wherein second layer of wireless hierarchical heterogeneous network is configured as a ub-net comprising multiplicity of sensors and actuators, wherein latency for servicing all devices located within said sub-net is smaller than scheduling period of first layer network hierarchy.

4. The system of claim 3, wherein sub-net of a second layer of a wireless hierarchical heterogeneous network is configured as a sub-system communicating with devices comprising said sub-system using digital wire interfaces and wherein said sub-system comprise of: a Bluetooth slave interface to first layer of network hierarch; a micro-controller (MCU); and a multiplicity of sensors and actuators.

5. The system of claim 3, wherein a sub-net of second layer of a wireless hierarchical heterogeneous network is configured as a sub-system communicating with devices comprising said sub-net using an ANT Personal Area Network (PAN) wireless interface, and comprising of: a Bluetooth slave interface communicating with first layer of network hierarchy; a control processor (MCU); and multiplicity of sensors and actuators.

6. The system of claim 5, wherein Bluetooth slave of sub-net performs master function of an ANT personal area network (PAN).

7. The system of claim 1, wherein control packet received from first layer of network hierarchy by Bluetooth slave of second layer of network hierarch located in sub-net is delivered to control processor (MCU), and wherein the MCU disassembles it's payload into control records dedicated to each individual device located within the sub-net, and wherein upon reception of said control record, the MCU performs all of the following:
  requests new data samples from each sensors identified in accelerometer control record then:
    for each sensor compares current data sample with previous data sample, and if difference between consecutive data samples is smaller then predefined minimum difference, replaces the current data sample with the 'zero' value, otherwise appends the current data sample to sensor data packet;
  transmits sensor data packet containing samples from all sensors identified in the accelerometer control record to the first layer of network hierarchy using Bluetooth slave-interface;
  for each actuator identified in the control record:
    extracts actuator control word;
    applies content of the actuator control word as an address to a Look-Up Table (LUT); and
    applies value stored in the LUT as a control signal to the actuator.

8. The system of claim 7, wherein actuator control record comprises: an actuator identifier; and a control word containing address to Look-up Table (LUT), stored in sub-system controller processor (MCU) memory, and wherein data stored in the LUT is in organized as M*N array, and contain an amplitude and frequency response of actuator control signal.

9. The system of claim 8, wherein address location of Look-up Table (LUT), included in actuator control word is obtained by calculating of a Mean Squared Error of a piece-wise fit between an optimal control signal and a impulse response of actuator control signal stored in the LUT.

10. The system of claim 8, wherein actuator control signal stored in Look-up Table (LUT), is applied directly to pulse-width-modulation (PDM), digital-to-analog (DAC), converter, and wherein density of '1s' included in actuator control signal defines actuator response time, while total number of '1s' the actuator control signal-amplitude.

11. The system of claim 8, wherein parameter N, associated with Look-up Table (LUT) depends on schedule period of first layer of network hierarchy and actuator response time and maximum amplitude.

12. A computer accessible non-transitory memory medium for storing program instructions configured to control a hierarchical network providing communication between smart-phone based analysis and control application and multiplicity of sensors and actuators configured as a sub-nets and embedded in ski equipment, wherein the program instructions execute all of the following:
  in each transmission time slot dedicated to Bluetooth master, using a Round-Robin scheduling method, the Bluetooth master sends to the selected sub-nets a control packet comprising control commands to all devices located within the selected sub-net;
  in each reception time slot dedicated to the Bluetooth master, the Bluetooth master receives sensor data packet from the selected sub-net, and if said data packet was not received, uses data packet received during previous scheduling period.

13. The method of claim 12, wherein control packet payload comprises:
  an accelerometer control record identifying individual sensors located within sub-net;
  a multiplicity of actuator control records; and
wherein size of said control packet is adjusted to a Bluetooth packet size by appending "0s" before said packet is encoded using forward error correction (FEC) code.

14. The method of claim 13, wherein accelerometer control record comprises identifiers of each sensor located within selected sub-net, and wherein said identification represents a request for data from the selected sensor.

15. The method of claim 13, wherein actuator control record comprises of an actuator identifier and an actuator control word; and wherein the actuator control word contains an address to look-up table (LUT), containing actuator control signal; and wherein address to the LUT is obtained by calculating a Mean Squared Error of piece-wise fit between an optimal control signal and impulse response stored in the LUT.

16. A computer accessible non-transitory memory medium for storing program instruction configured to control network hierarchy and to provide communication between smart-phone based analysis and control application and multiplicity of sensors and actuators configured as sub-nets embedded in ski equipment, wherein program instructions execute all of the following:

for each control packet received from Bluetooth master, sub-net control processor performs the following:
        for each sensors identified in accelerometer record:
            retrieves sensor data samples;
            compares current data sample with previous data sample, and if difference between said consecutive samples is smaller than predefined threshold, replaces the current data sample with 'zero' value;
            assembles data samples received from all sensors into a sensor data packet, and if said sensor data packet contains values other than 'zeros' sends the sensor data packet to the Bluetooth slave located within the sub-net for transmission to the Bluetooth master, otherwise disables slave transmission;
        for each actuator identified in the control packet:
            retrieves actuator control word:
            applies the actuator control word as address Look-Up Table (LUT), then uses value stored in the LUT as a control signal for the actuator identified in the actuator control packet.

17. The method of claim 16, wherein communication between all devices located within sub-net is conducted using a digital wire interface.

18. The method of claim 16, wherein communication between all devices located within sub-net is conducted using an ANT personal network wireless (PAN) radio interface.

19. The method of claim 16, wherein actuator control signal stored in sub-net control processor Look-Up-Table (LUT) is applied directly to pulse-width-modulation (PDM) digital-to-analog converter (DAC), as a control voltage of selected actuator.

* * * * *